(12) United States Patent
Nishiyama et al.

(10) Patent No.: US 7,463,350 B2
(45) Date of Patent: Dec. 9, 2008

(54) METHOD AND APPARATUS FOR DETECTING DEFECTS OF A SAMPLE USING A DARK FIELD SIGNAL AND A BRIGHT FIELD SIGNAL

(75) Inventors: Hidetoshi Nishiyama, Fujisawa (JP); Minoru Yoshida, Yokohama (JP); Yukihiro Shibata, Fujisawa (JP); Shunji Maeda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 291 days.

(21) Appl. No.: 10/981,721

(22) Filed: Nov. 5, 2004

(65) Prior Publication Data
US 2005/0110988 A1    May 26, 2005

(30) Foreign Application Priority Data
Nov. 5, 2003    (JP)    ............... 2003-375093
Jan. 7, 2004    (JP)    ............... 2004-001603

(51) Int. Cl.
G01N 21/00    (2006.01)
(52) U.S. Cl. .................................. 356/237.4
(58) Field of Classification Search .............. 356/450, 356/491, 495, 516, 237.4, 237.5
See application file for complete search history.

(56) References Cited

U.S. PATENT DOCUMENTS

| | | | |
|---|---|---|---|
| 6,256,087 B1 * | 7/2001 | Bader | 355/67 |
| 6,384,910 B2 * | 5/2002 | Vaez-Iravani et al. | 356/237.4 |
| 6,556,290 B2 * | 4/2003 | Maeda et al. | 356/237.5 |
| 7,030,978 B2 * | 4/2006 | Guetta et al. | 356/237.5 |
| 2003/0011760 A1 * | 1/2003 | Vaez-Iravani et al. | 356/237.2 |
| 2003/0081201 A1 * | 5/2003 | Shibata et al. | 356/237.2 |
| 2004/0145734 A1 * | 7/2004 | Shibata et al. | 356/237.5 |

FOREIGN PATENT DOCUMENTS

| | | |
|---|---|---|
| JP | 61-212708 | 9/1986 |
| JP | 07-318326 | 12/1995 |
| JP | 08-320294 | 12/1996 |
| JP | 10-078668 | 3/1998 |
| JP | 2000-155099 | 6/2000 |
| JP | 2001-194323 | 7/2001 |

* cited by examiner

Primary Examiner—Samuel A Turner
(74) Attorney, Agent, or Firm—Antonelli, Terry, Stout & Kraus, LLP.

(57) ABSTRACT

Disclosed is a method and apparatus for inspecting defects of patterns of a sample at high speed and with high sensitivity while damage of the sample arising from high-power pulsed light is reduced. Light emitted from a pulsed laser light source is transmitted through a pseudo continuous-wave forming optical system having an optical system capable of reducing energy per pulse and yet maintaining the entire amount of light of the pulsed light, a beam formation optical system, and a coherence reduction optical system, and a beam deflected by a deformation illumination optical system is made to reflect on a PBS to be irradiated on a wafer. The apparatus is configured so that the diffracted light from the wafer is focused by an objective lens, transmitted through light modulation units, focused to form a plurality of images on a plurality of image sensors in a visual-field divided parallel detection unit 12, and then defects are detected by a signal processing unit.

9 Claims, 29 Drawing Sheets (a)

(b)

(a)

(b)

(a)

(b)

(a)

(b)

(a)

(b)

(a)

(b)

(a)

(b)

(a)

(b)

Range of small intensity change against film thickness change

(a)
Front view

(b)
Plan view

METHOD AND APPARATUS FOR DETECTING DEFECTS OF A SAMPLE USING A DARK FIELD SIGNAL AND A BRIGHT FIELD SIGNAL

BACKGROUND OF THE INVENTION

The present invention relates to pattern defect inspection and foreign material inspection to detect such defects of a circuit pattern of a sample as shortage, breaking of wire and foreign matters. The invention particularly relates to a method and an apparatus for inspecting defects and foreign matters in such circuit pattern as of a semiconductor wafer, a liquid display, a photomask. In the description below, defects shall include foreign matters.

Conventionally, as this type of inspection apparatus, there is one that picks up an image of a sample using an imaging device, such as an image sensor, while moving the sample, and compares a detected image signal and that signal delayed by a fixed time, and thereby perceives a part in which the two image signals are not in agreement as a defect.

As another technology related to defect inspection of a sample, there is a technology of performing accurate inspection in a semiconductor wafer where an area of high pattern density, such as a memory mat part, and an area of low pattern density, such as a peripheral circuit, exist together in the same die. This technology is one that performs gray-scale translation on a digital image signal obtained by A/D converting a detected signal so that brightness values or contrast values of the high-density area and the low-density area of the pattern under inspection assume a predetermined relation, and compares the image signal whose gray scale was translated and an image signal for comparison whose gray scale was translated with physical positions of the two signals aligned.

As a technology of inspecting a circuit pattern of a photomask, there is a technology in which UV (UltraViolet) laser light is used as a light source, a mask is uniformly illuminated with light whose coherence is reduced by rotating a diffuser plate that is inserted in its optical path, feature quantities are calculated from obtained image data of the mask, and thereby the quality of the mask is determined.

As conventional technologies related to this invention, there are ones that are disclosed in JP 318326-H07A, JP 320294-H08A, JP 78668-H10A, JP 212708-S61A, JP 155099-2000A, and JP 194323-2001A, etc.

In LSI manufacture in recent years, circuit patterns formed on wafers have pattern widths equal to or less than 200 nm because of pattern miniaturization that corresponds to the need of higher integration, and accordingly dimensions of defects to be detected becomes finer. Especially, there is also reported a defect, called "Non Visual Defect," that is hard to detect by the conventional technology. Under these circumstances, for defect detection apparatuses, development aiming at an objective lens for inspection with a higher NA (Numerical Aperture) and a super resolution technology has been advanced. However, since the higher NA of the objective lens for inspection has reached its physical limit, it is an essential approach to shorten the wavelengths of illumination light used for inspection toward regions of UV light and DUV (Deep UltraViolet) light.

Light sources of short wavelengths may include the UV light, the DUV light, VUV (Vacuum UltraViolet) light etc. However, under the present circumstances, they are generated mainly by pulsed lasers. However, the pulsed lasers have high peak powers, so it is very likely that a sample irradiated by that laser light might be damaged. Therefore, it can be considered that a laser with a reduced power level is used. However, in this case, it is necessary to lengthen storage time of an image sensor for detecting reflected light because of insufficient amount of light irradiated on the sample, and hence this measure comes with a problem of incompatibility with high-speed inspection.

When high-speed inspection is intended, an illumination method of scanning a narrowly converged laser beam on a sample is not suitable. Conversely, if a laser beam that is expanded as large as the whole visual field is used for illumination, there occurs speckle by the laser and signals of overshoot and undershoot, called ringing, are generated in edge parts of a circuit pattern; therefore, it is difficult to obtain a high-quality image, and otherwise it is necessary to reduce interference by the laser light.

Moreover, in the LSI device, structures of patterns to be inspected have become complicated and diversified, such as memory products formed mainly with a repeated pattern and logic products formed mainly with a non-repeated pattern, so it is difficult to find targeted defects surely. Furthermore, in the process of metal wiring, such as of Al (aluminum), minute irregularities called grain, pit, and morphology occur. Because this grain is detected as an optical noise during inspection, there is a problem that detected grain must be reduced. Moreover, in any process in which a transparent film (here, a term transparent is used to mean "being transparent at illumination wavelength"), such as an insulator film, is exposed as an uppermost layer, interference-light intensity unevenness arising from a minute difference in thickness of the transparent film causes optical noise. Therefore, there is a problem that the optical noise must be reduced.

SUMMARY OF THE INVENTION

One preferred aspect of the present invention resides in an apparatus for inspecting defects of patterns, and the apparatus has: an illumination light source of pulsed oscillation; a pseudo continuous-wave forming unit that averages the amount of light of the illumination light source; a beam forming unit that adjusts a beam shape of the illumination light emitted from the pseudo continuous-wave forming unit; a coherence reducing unit that suppresses coherence of the illumination light adjusted by the beam forming unit; a deformation illuminating unit that deflects the illumination light emitted from the coherence reducing unit; an irradiating unit that irradiates on a sample the illumination light deflected by the deformation illuminating unit; an image forming unit that focuses the reflected light from the sample illuminated by the irradiating unit to form an image; a light modulating unit that controls the diffracted light used for illumination and detected; an image detecting unit that divides an image of the sample formed by the image forming unit and detects image signals picked up by a plurality of sensors; and a defect detecting unit that detects defects of a pattern formed on the sample based on the detected signals detected by the image detecting unit.

According to this invention, damage on the wafer caused by the illumination light can be reduced, the coherence of the laser light can be reduced, and further output of the grain can be stabilized while reducing amount-of-light unevenness from a part of the insulator film in the wiring process etc. In addition, it becomes possible to perform parallel detection by dividing a range of visual field without causing a loss, and hence high-speed and high-sensitivity inspection of a wafer in each step becomes possible.

These and other objects, features and advantages of the invention will be apparent from the following more particular description of preferred embodiments of the invention, as illustrated in the accompanying drawings.

BRIEF DESCRIPTION OF THE DRAWINGS

FIG. 3 is a diagram of pseudo continuous-wave light with a reduced peak output.

DESCRIPTION OF THE PREFERRED EMBODIMENTS

Embodiments in which this invention is carried out will be explained below.

Figure 1:
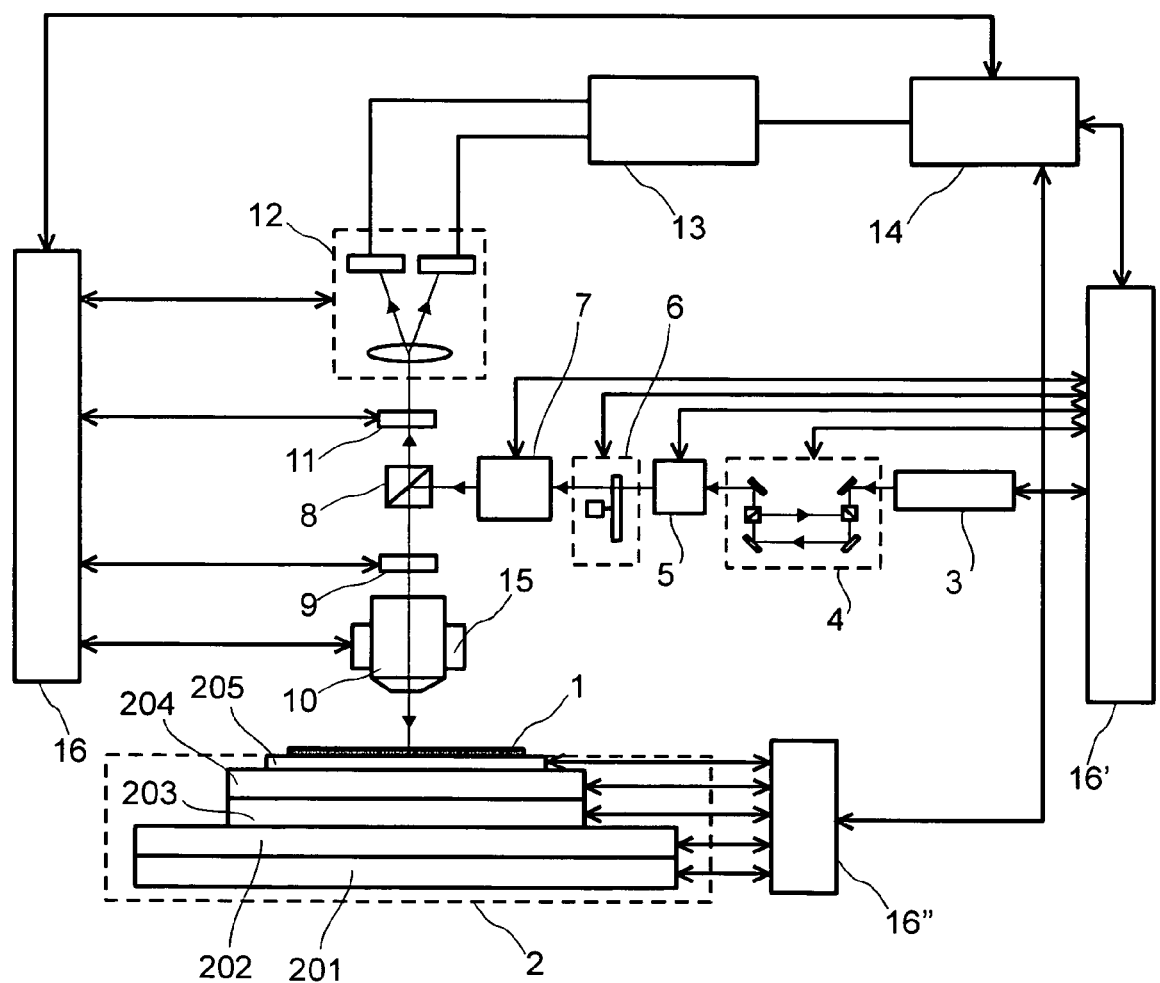
FIG. 1 is a block diagram showing an embodiment of this invention.

An embodiment of a pattern-defect inspection apparatus according to this invention is shown in FIG. 1. The pattern-defect inspection apparatus of this invention consists of: a conveyance system 2 for placing and moving a wafer 1 to be inspected, an illumination light source 3, a pseudo continuous-wave forming optical system 4, a beam formation optical system 5, a coherence reduction optical system 6, a deformation illumination optical system 7, a polarizing beam splitter (hereafter referred to as PBS) 8, a light modulation unit A 9, an objective lens 10, a light modulation unit B 11, a visual-field divided parallel detection unit 12, a signal processing circuit 13, an I/O unit 14, an automatic focusing unit (hereinafter referred to as A/F unit) 15, controllers 16, 16', and 16" of the units, and relay lenses and mirrors not shown in the figure.

Next, its operation will be described. Illumination light emitted from the illumination light source 3 enters the pseudo continuous-wave forming optical system 4, and is converted to light whose amount of light is averaged or almost equalized temporally. The illumination light emitted from the pseudo continuous-wave forming optical system 4 enters the beam formation optical system 5, where its beam diameter and illuminance distribution are adjusted. The illumination light emitted from the beam formation optical system 5 enters the coherence reduction optical system 6, where its temporal and spatial coherence is reduced. The illumination light emitted from the coherence reduction optical system 6 is made to change its illuminance distribution in a pupil position of the objective lens 10 by the deformation illumination optical system 7. The S-polarization component of the illumination light emitted from the deformation illumination optical system 7 is reflected to the objective lens 10 side by the PBS 8, transmitted through the light modulation unit A 9 and the objective lens 10, and irradiated on the wafer 1.

The illumination light reflected on the wafer 1 is transmitted through the objective lens 10 and the light modulation unit A 9, and enter the PBS 8. The P-polarization component of the incident light is transmitted through the PBS 8 and the light modulation unit B 11, and forms an image on an image sensor in the visual-field divided parallel detection unit 12. The image sensor converts it to an image signal. The converted image signal is subjected to defect detection processing in the signal processing circuit 13, which detects defects on the wafer 1. Inspection results are inputted into the I/O unit 14 and displayed on a screen. The whole surface of the wafer 1 is inspected by performing the above operation while the wafer 1 is being moved. This I/O unit 14 has an interface function of receiving input information from the user, and enables transmission and reception of control signals to the controllers 16, 16', and 16". Moreover, the A/F unit 15 emits a signal for moving the wafer 1 to an object-side focal position of the objective lens 10, and controls the conveyance system 2 with the controller 16" to move the wafer 1 in real time.

Details of each part will be described below.

First, the conveyance system 2 consists of an X-axis stage 201, an Y-axis stage 202, a Z-axis stage 203, a θ-axis stage 204, and a wafer chuck 205. The X-axis stage 201 is constructed to be able to travel at a constant speed, and the Y-axis stage is constructed to be able to move stepwise. By using the X-axis stage 201 and the Y-axis stage 202, all locations in the wafer 1 can be moved to just under the center of the objective lens 10. The Z-axis stage 203 has a function of moving the wafer chuck 205 vertically, and the θ-axis stage 204 has a function of rotating the wafer chuck 205 to effect alignment of the traveling directions of the X-axis stage 201 and the Y-axis stage 202 with the rotation direction of the wafer 1. In addition, the wafer chuck 205 has a function of fixing the wafer 1 by sucking it by means of vacuum etc.

The illumination light source 3 is a laser light source, such as of ultraviolet light (hereinafter referred to as UV light), deep ultraviolet light (hereinafter referred to as DUV light), vacuum ultraviolet light, and extreme ultraviolet light, and an oscillation mode of the laser may be either continuous oscillation or pulsed oscillation. It is preferable that the wavelength of the illumination light source 3 is in general 400 nm or less, and light sources of, e.g., 355 nm, 266 nm, 157 nm, and 130 nm are applicable. For the laser light source, a laser system for emitting the third harmonic or the fourth harmonic of a fundamental wave of a solid-state YAG laser (wavelength 1024 nm) by converting its wavelength with a nonlinear optical crystal etc., and excimer lasers and ion lasers of a wavelength of 248 nm etc. may be used. A light source for emitting multiwavelength light (e.g., 351 nm, 248 nm, 193 nm, 172 nm, 157 nm, 147 nm, 126 nm, 121 nm, etc.), such as electron-beam-gas-emission-lamp, is also usable. For pulsed lasers, a low pulse-repetition-frequency pulsed laser of a pulse repetition frequency of a few Hz may be usable, and quasi-continuous oscillation pulsed laser of tens of hertz, such as of the mode-locking type, may be usable.

The merit of these light sources is that with the use of a short wavelength light source, resolution of the optical system is increased, and hence high-sensitivity inspection can be expected. Moreover, since solid-state lasers, such as YAG, do not require large equipment, a scale of the apparatus can be made small at low cost. When a high pulse-repetition-frequency pulsed laser is used, it can be handled in the same manner as a high-output continuous oscillation laser; therefore, it becomes possible to use low-price optical components with low transmittance or reflectance, and an inexpensive apparatus can be realized. The embodiment will be described below as the case where a pulsed laser is used for the illumination light source 3.

Figure 2:
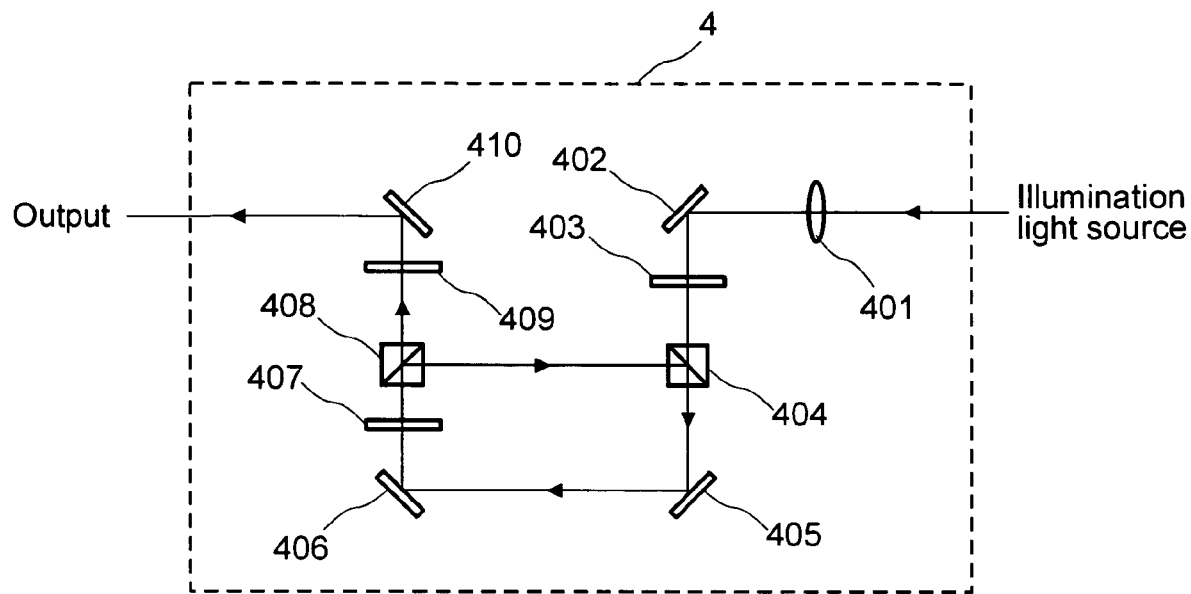
FIG. 2 is a view showing a configuration of a pseudo continuous-wave forming optical system.

Details of the pseudo continuous-wave forming optical system 4 will be described using FIG. 2. The purpose of the pseudo continuous-wave forming optical system 4 is that pulsed light of a large peak power is divided temporally and moved in a time base to reduce the maximum amount of light (a peak value of the amount of light) while maintaining the total amount of light per unit time, that is, the intensity is reduced while the amount of illumination light irradiated on the wafer 1 per unit time is not changed. With this system, damage to the wafer 1 can be made small compared with the case where pulsed light of a large peak power is irradiated on the wafer 1.

The pseudo continuous-wave forming optical system 4 consists of a collimator lens 401, mirrors 402, 405, 406, and 410, half-wave plates 403, 407, and 409, and PBSs 404, 408. Illumination light emitted from the illumination light source 3 is converted to parallel light by the collimator lens 401. The parallel light is reflected by the mirror 402, and its polarization direction is changed by the half-wave plate 403. The half-wave plate 403 rotates the polarization direction of the parallel light to a direction (P-polarized light) in which the parallel light is allowed to pass through the PBS 404.

The light transmitted through the PBS 404 is reflected by the mirrors 405, 406, and its polarization direction is changed by the half-wave plate 407. This half-wave plate 407 is used to alter the ratio of the transmitted light and the reflected light at the PBS 408. Here, it is preferable to set the polarization direction after rotation by the half-wave plate 407 to a direction in which 50% of the light is allowed to pass through the PBS 408. The light (P-polarized light) transmitted through the PBS 408 is reflected by the mirror 410 through the half-wave plate 409, and outputted from the pseudo-continuous-wave forming optical system 4.

Figure 3:
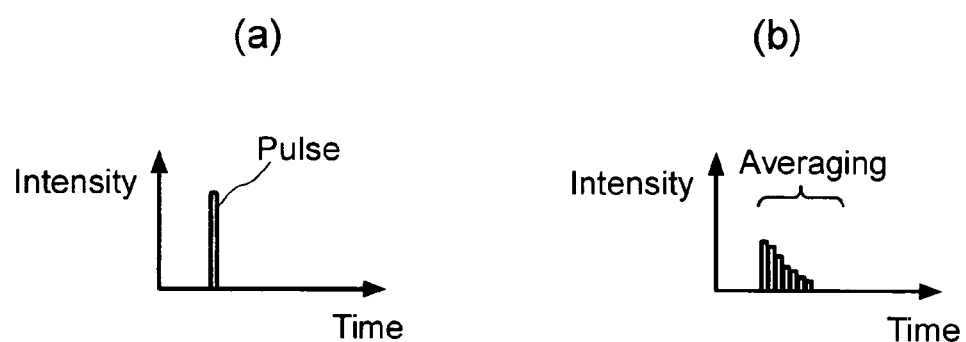
FIG. 3 is a diagram of incident pulsed light to show the effect of a pseudo continuous-wave forming optical system.

On the other hand, the light (S-polarized light) reflected by the PBS 408 enters the PBS 404, is reflected in the direction of the mirror 405, and enters the PBS 408 again through the mirrors 405, 406 and the half-wave plate 407. Therefore, 50% of the light that entered the PBS 408 again will be outputted from the pseudo continuous-wave forming optical system 4. By repeating these operations, incident pulsed light as shown in FIG. 3A that is emitted from the illumination light source and entered the pseudo-continuous-wave forming optical system 4 is averaged temporally, converted to pseudo continuous-wave light with a reduced peak output as shown in FIG. 3B, and outputted from the pseudo continuous-wave forming optical system 4.

Figure 4:
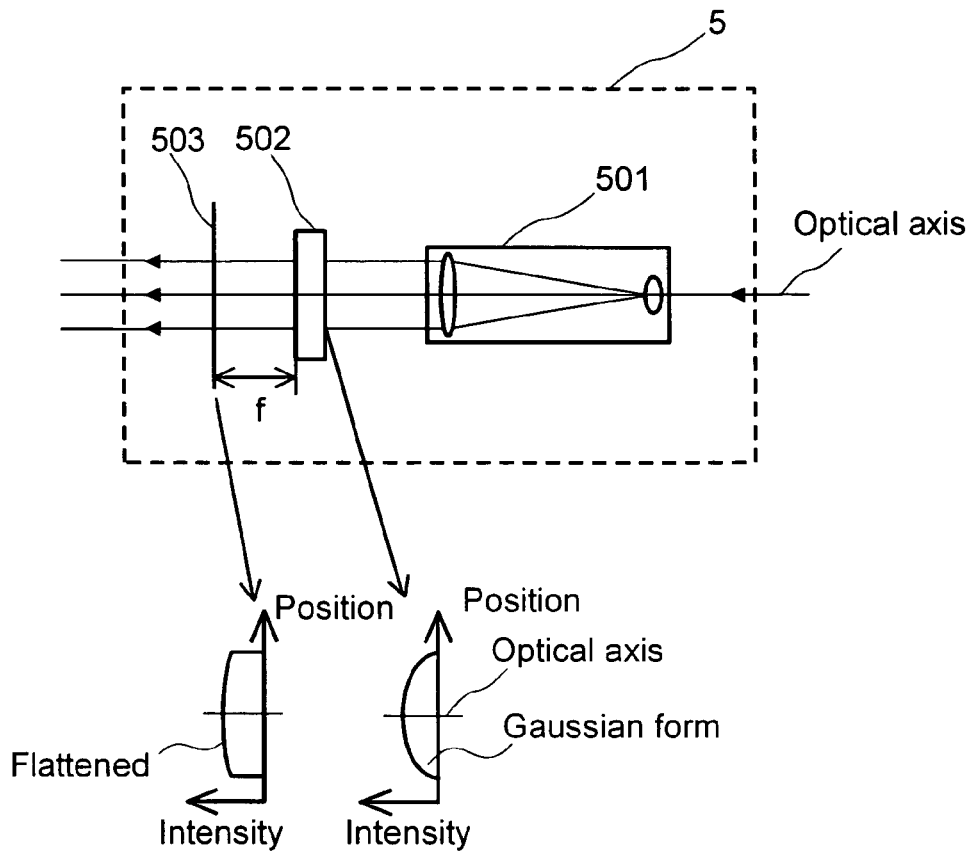
FIG. 4 is a view showing a configuration of a beam formation optical system.
Figure 5:
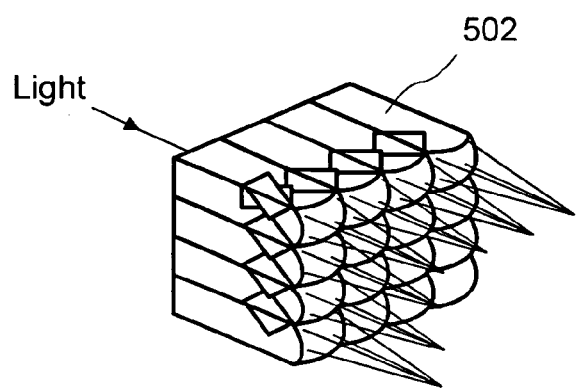
FIG. 5 is a schematic diagram showing a laser intensity distribution averaging optical element.

Next, details of the beam formation optical system 5 will be described using FIG. 4. The purpose of the beam formation optical system 5 is to flatten the illuminance distribution of the illumination light. The beam formation optical system 5 consists of a beam expander 501 and a laser intensity-distribution averaging optical element 502. A function of the beam formation optical system 5 is to expand the incident light with the beam expander 501, form a plurality of beam spots with the laser intensity-distribution averaging optical element 502 as shown in FIG. 5 and flatten the distribution of intensity of the beam in a focal position 503 of the laser intensity-distribution averaging optical element 502. If the beam expander 501 is equipped with a zoom mechanism, it brings an advantage that many kinds of illuminations can be formed. For example, σ of illumination can be changed by changing a magnification with the zoom mechanism.

Here, the laser intensity-distribution averaging optical element 502 has an appearance, for example, shown in FIG. 5. This is an optical element for forming point light sources in focal positions of the group of lenses by arranging a plurality of lenses, and includes a fly array lens etc.

Figure 6:
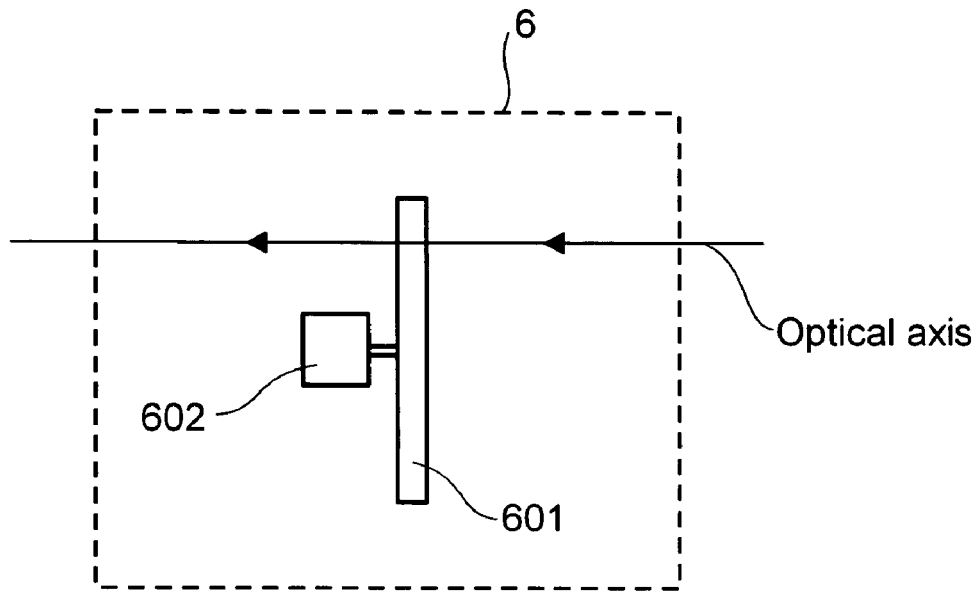
FIG. 6 is a view showing a configuration of a coherence reduction optical system.

Details of the coherence reduction optical system 6 will be described using FIG. 6. The purpose of the coherence reduction optical system 6 is to reduce the coherence of a laser temporally and spatially. For this purpose, the coherence reduction optical system 6 consists of a phase fluctuating plate 601 and a motor 602 which rotates the phase fluctuating plate 601. Its function is to output a beam inputted into the coherence reduction optical system 6 after transmitting it through the phase fluctuating plate 601 that is rotated by the motor 602.

Figure 7:
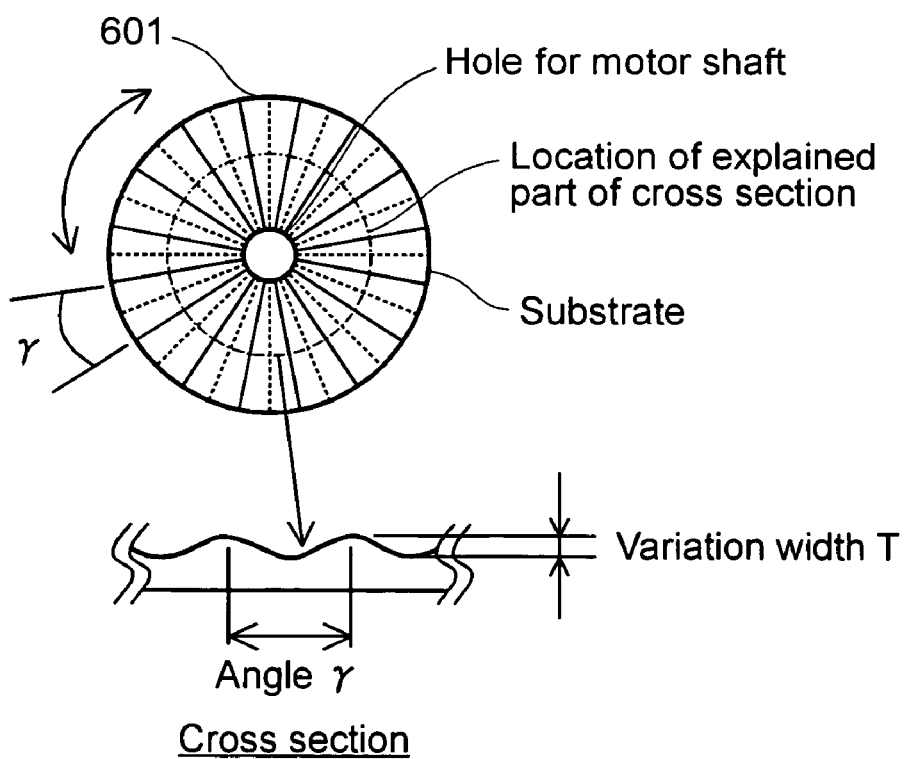
FIG. 7 is a view showing a phase fluctuating plate.

FIG. 7 shows an appearance of the phase fluctuating plate 601. As shown in FIG. 7, the phase fluctuating plate 601 varies the phase of the transmitted light by changing the thickness of its substrate through which light of the illumination wavelength pass (e.g., a plate of silica or quartz in the case of the illumination light source of a wavelength of 266 nm), and has a hole for a shaft of the motor in its center. More specifically, a plate whose cross sectional in the circumferential direction varies continuously in a sinusoidal manner is desirable. Moreover, preferably a variation of the plate thickness is larger than the illumination wavelength. Furthermore, it is good that the period of the sinusoidal shape satisfies the following condition (Formula 1). In Formula 1, a storage time of the image sensor (TDI: Time Delay Integration; in the case of an integration type sensor: [storage time of one stage] times [the number of storage stages]) is indicated by S [s], an angle of one period of the sinusoidal shape by γ[rad], and a rotational angular speed of the phase fluctuating plate 601 by ω[rad/s].

$$S/(\gamma/\omega)=n \qquad \text{(Formula 1)}$$

Here, n is an integer of unity or more.

Figure 8:
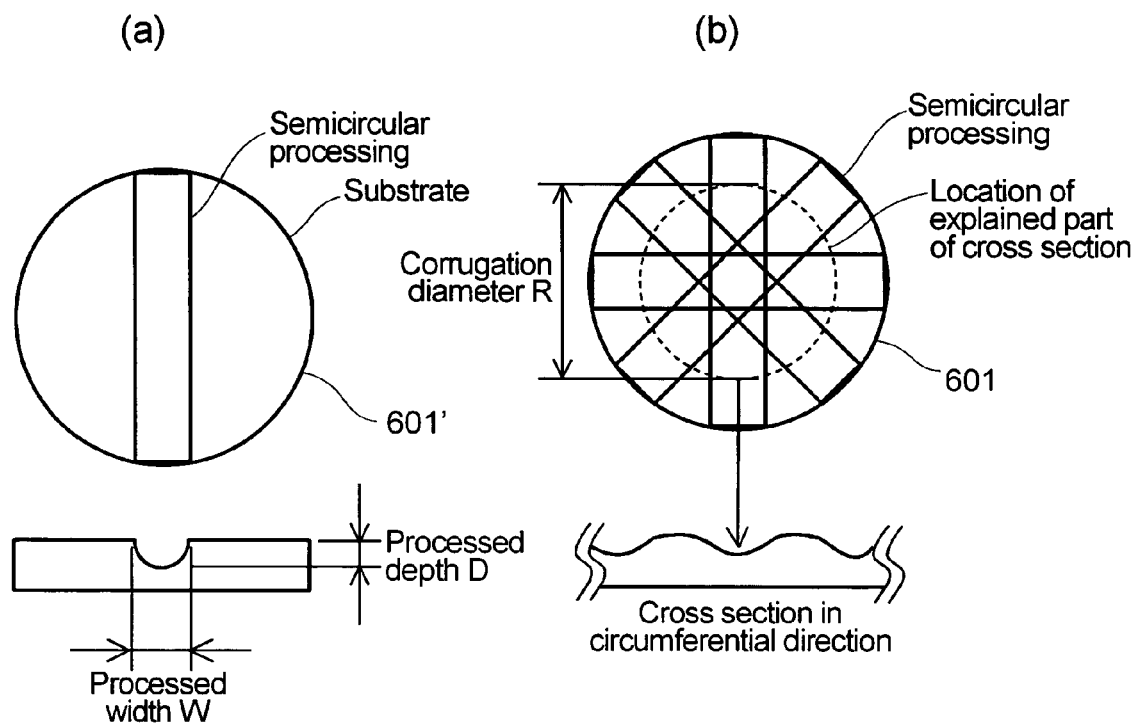
FIG. 8A is a schematic diagram of a circular quartz substrate on which a semicircular cross-section recess was processed to show one example of a manufacturing method of the phase fluctuating plate.
FIG. 8B is a schematic diagram of a circular quartz substrate on which semicircular cross-section recesses were processed.

One example of a manufacturing method of the phase fluctuating plate 601 will be described using FIG. 8. FIG. 8A shows a circular quartz substrate 601' on which a semicircular cross-section recess was processed. At this time, the processed depth D is a variation T of the above-mentioned plate thickness and the processed width W is determined by Formula 2 that will be described later. If these semicircular cross-section recesses are processed on locations that are rotated by a fixed angle with the center of the circular plate being set as a center of rotation, it will have the form of FIG. 8B. When processing it by this method, the place where a cross section takes a sinusoidal shape is a certain circular portion. Therefore, it is necessary to determine in advance the location in which the sinusoidal shape is intended to be formed (R in FIG. 8B).

$$W=\pi*R/K \qquad \text{(Formula 2)}$$

Here, π is the circular constant, R is a diameter of a circle in which the sinusoidal shape is made, and K is the number of the sinusoidal shape on the circle.

Although in this embodiment, an example of manufacturing it by machining was explained as a manufacturing method of the phase fluctuating plate 601. However, the manufacturing method is not limited to this; processing by etching may be used, an optical path length may be changed by depositing a dielectric film, such as of SiO2, and it may be manufactured by direct drawing with an electron beam. An advantage of each manufacturing method is as follows: The machining enables easy and inexpensive manufacture. By the etching, the first phase fluctuating plate is expensive due to mask manufacture, but the second and subsequent plates can be manufactured inexpensively, and the etching can handle more complicate processing than the machining does. When manufacturing it with a dielectric film, a smooth sinusoidal shape can be manufactured and a phase can be varied almost continuously. The direct drawing system is also capable of complicated processing.

Figure 9:
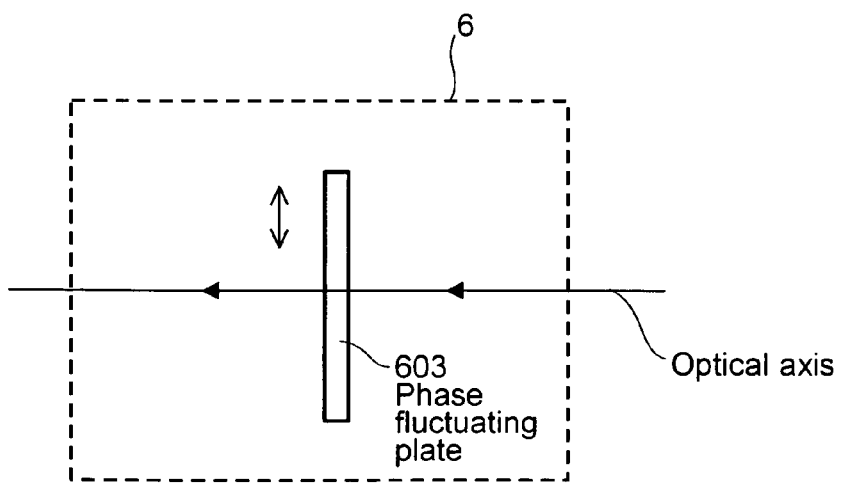
FIG. 9 is a view showing another example of the coherence reduction optical system.
Figure 10:
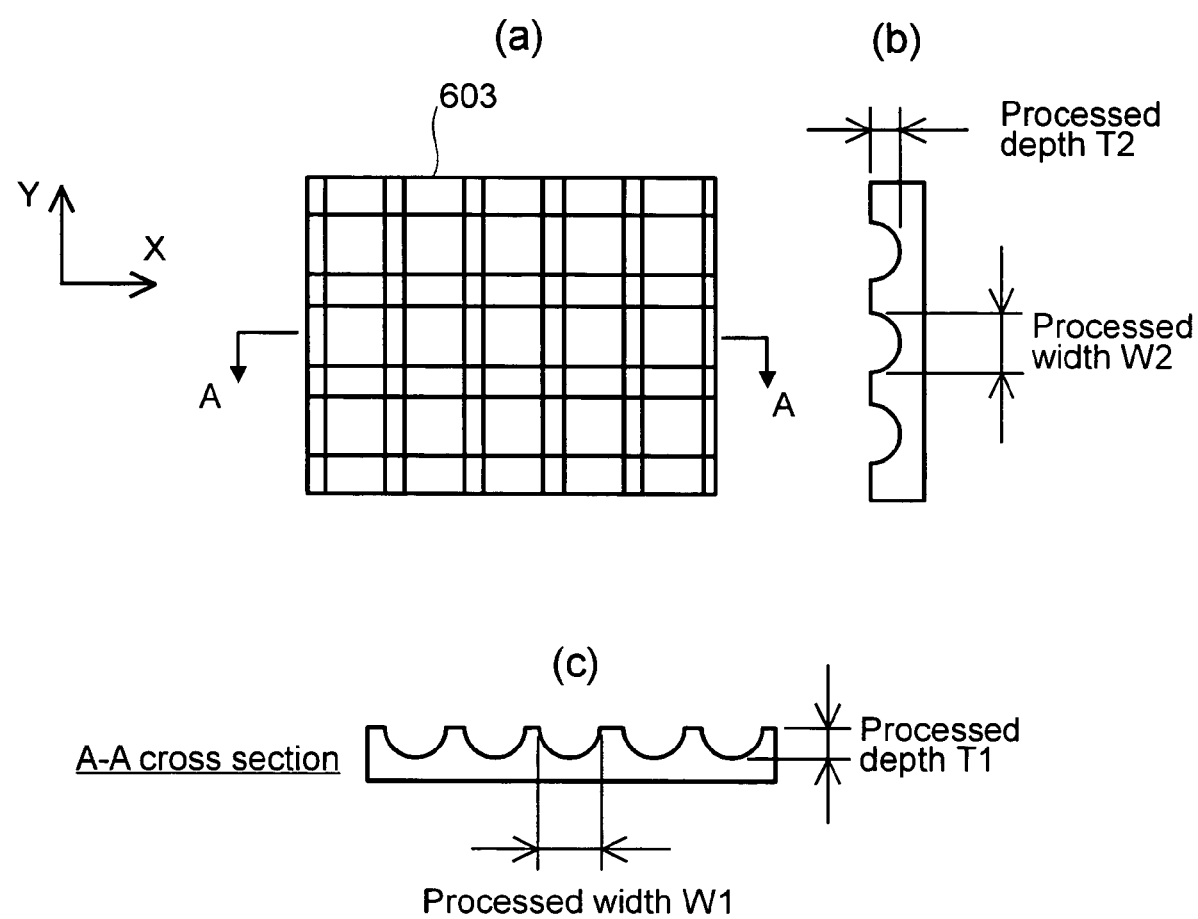
FIG. 10A is a plan view of the phase fluctuating plate to show another example of the phase fluctuating plate.
FIG. 10B is a side view of the phase fluctuating plate.
FIG. 10C is a side view of the phase fluctuating plate.

FIG. 9 shows another embodiment of the coherence reduction optical system 6. Shown in FIG. 9 is a method of oscillating a phase fluctuating plate 603 in a direction perpendicular to the optical axis (an oscillating unit being not shown in the figure), and the phase fluctuating plate 603 oscillates for one period or more within a storage time of the image sensor. FIG. 10 shows one example of the manufacturing method of the phase fluctuating plate 603. In this method, since it is necessary only to oscillate the phase fluctuating plate 603, all that is required is to perform semicircular cross-section processing on a rectangular transparent substrate. This method has an advantage that two-dimensional processing, namely, two-dimensional phase fluctuation can be realized easily. FIG. 10A is a plan view of the phase fluctuating plate 603, and FIG. 10B and FIG. 10C are side views, respectively.

Figure 11:
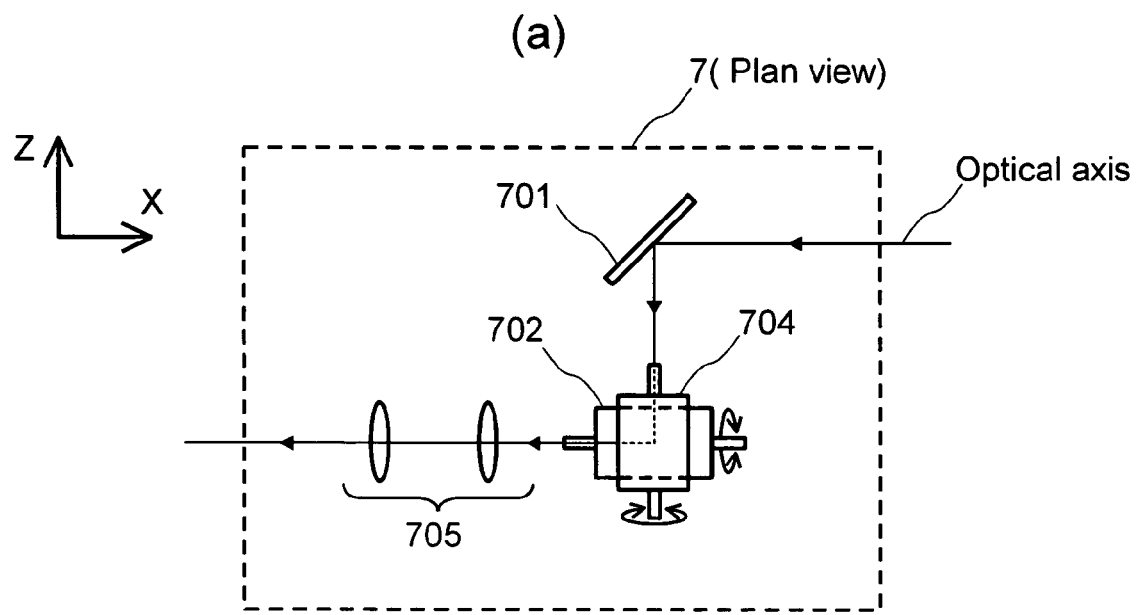
FIG. 11A is a plan view of the deformation illumination optical system to show a configuration thereof.
FIG. 11B is a front view of the deformation illumination optical system.
Figure 11:
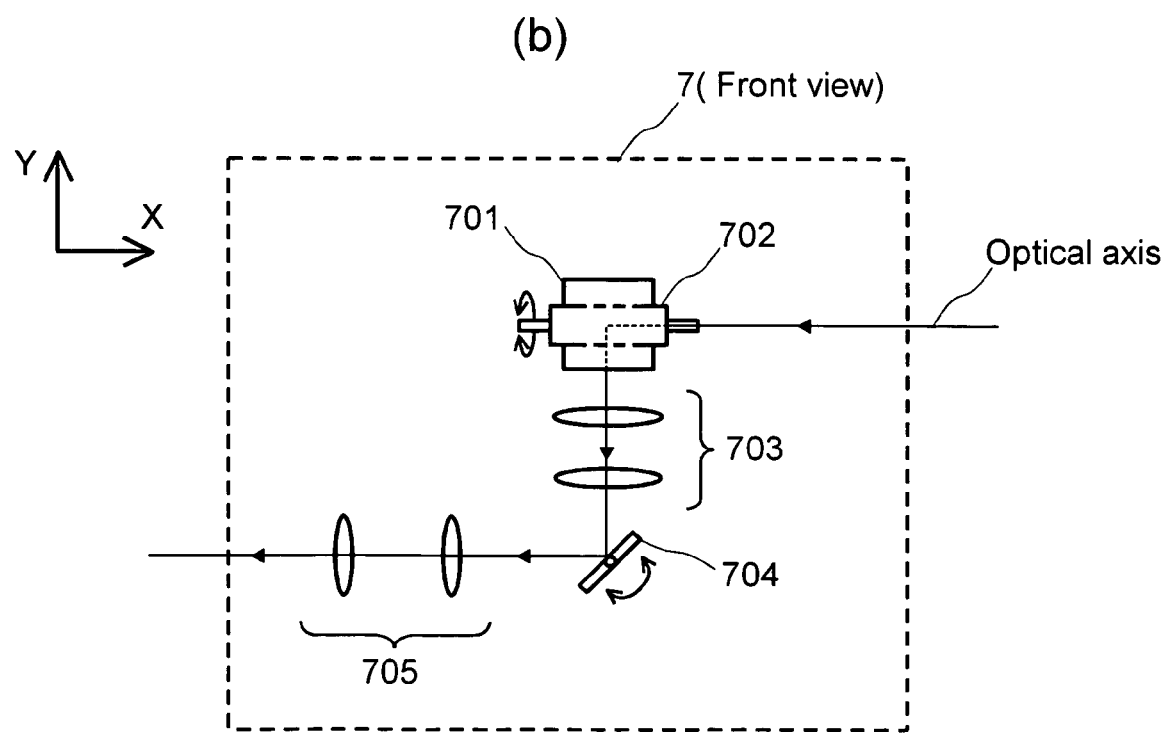

Details of the deformation illumination optical system 7 will be described using FIG. 11. FIG. 11A is a plan view of the deformation illumination optical system 7 and FIG. 11B is a front view thereof. The purpose of the deformation illumination optical system 7 is to perform illumination that can support various process wafers by changing the illuminance distribution of the illumination light in the pupil position of the objective lens 10. The deformation illumination optical system 7 consists of a fixed mirror 701, oscillating mirrors 702, 704, and relay lenses 703, 705. Next, its operation will be described.

The light that entered the deformation illumination optical system 7 from the direction of the X-axis is reflected in the direction of the Z-axis by the fixed mirror 701. The reflected light is deflected in the Y-Z plane by the oscillating mirror 702 that oscillates about the X-axis. The deflected light is transmitted through the relay lens 703, and is incident on the oscillating mirror 704 that oscillates about the Z-axis. The incident light is deflected in the X-Y plane by the oscillating mirror 704. The deflected light is emitted from the deformation illumination optical system 7 by the relay lens 705. Here, for the oscillating mirrors 702, 704, it is recommended to use, for example; a galvanometer mirror and a semiconductor resonant mirror. In the case where an oscillating frequency necessary for the oscillating mirror is low and generally a few hundreds of Hz or lower is required, the galvanometer mirror is allowed to use, which brings an advantage of manufacturing a low-cost apparatus. In the case where a high frequency is required, the semiconductor resonant mirror should be used.

Figure 12:
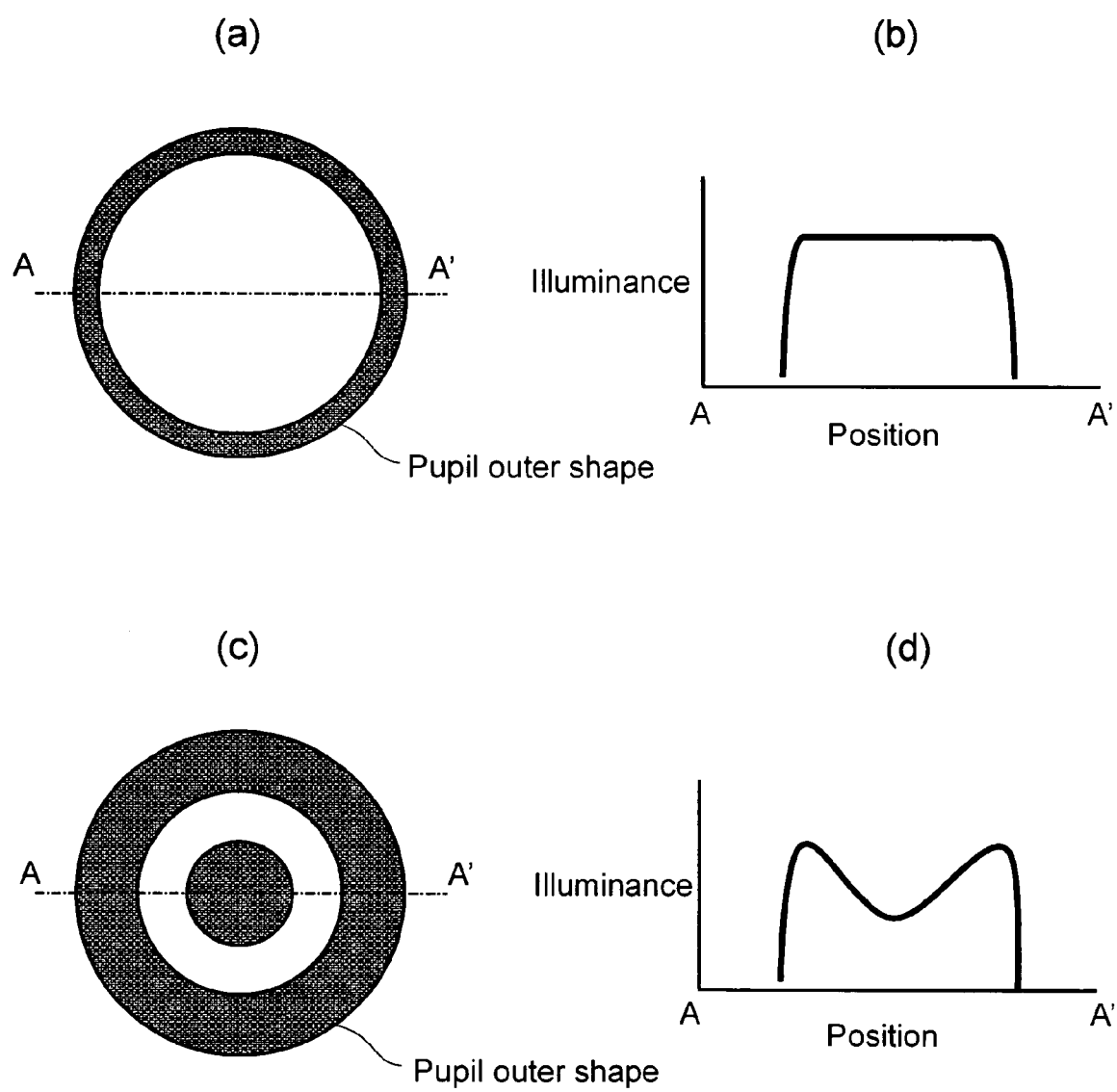
FIG. 12A is a schematic diagram of an illuminance distribution in a pupil position of the objective lens in the case where both oscillating mirrors are stopped to show the relation between the oscillating mirrors and the illuminance distribution.
FIG. 12B is a diagram of the illuminance distribution of FIG. 12A.
FIG. 12C is a schematic diagram of the illuminance distribution in the case where both oscillating mirrors are oscillated with the same timing.
FIG. 12D is a diagram of the illuminance distribution of FIG. 12C.

Next, an example of the illuminance distribution in the pupil position of the objective lens 10 dependent on an oscillation mode of the oscillating mirrors 702, 704 will be described using FIG. 12. FIG. 12A shows the case where both of the oscillating mirrors 702, 704 are stopped (being not allowed to oscillate). In this case, the illuminance distribution in the pupil position becomes a shape that is widened in its pupil central part as shown in FIG. 12B. FIG. 120 is the case where the oscillating mirrors 702, 704 are oscillated with the same timing. In this case, the illuminance distribution in the pupil position becomes a circular illuminance distribution as shown in FIG. 12D, i.e., a ring illuminance distribution. Making the illumination shape different has the following respective advantages: the shape in FIG. 12A enables the illumination light to efficiently illuminate a sample; and the shape in FIG. 12C enables high-order diffracted light from the wafer 1 to be detected, so the resolution of the pattern on the wafer can be increased.

Figure 13:
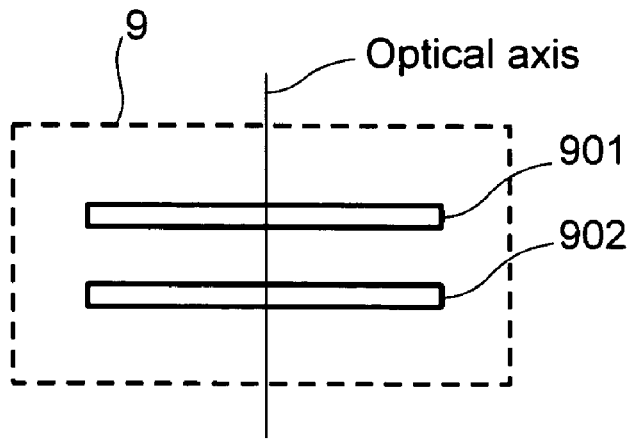
FIG. 13 is a view showing a configuration of a light modulation unit A.
Figure 14:
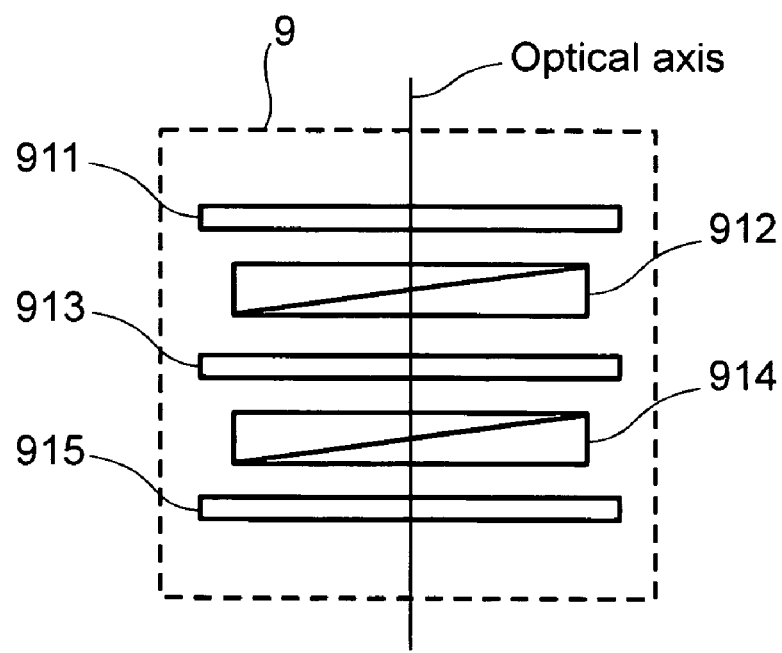
FIG. 14 is a view showing a configuration of a differential interference optical system.

FIG. 13 and FIG. 14 are used to explain details of the light modulation unit A 9. The light modulation unit A 9 is a unit for adjusting, for example, the ratio of the amount of light between the zero-order diffracted light and the high-order diffracted light both reflected from the wafer 1, being a unit for improving the contrast of the circuit pattern signal detected by the visual-field divided parallel detection unit 12. Alternatively, it is a unit for improving the contrast of a circuit pattern by polarization differential interference.

FIG. 13 shows an example of a unit for adjusting the ratio of the amount of light between the zero-order diffracted light and the high-order diffracted light. The unit in FIG. 13 consists of a half-wave plate 901 and a quarter-wave plate 902. The illumination light emitted from the deformation illumination optical system 7 enters the PBS 8, and the S-polarized light (linearly polarized light) thereof is reflected and enters the half-wave plate 901. The half-wave plate 901 converts the S-polarized light to a linearly polarized light whose azimuthal angle is rotated. Moreover, the linearly polarized light is converted to elliptically polarized light by being transmitted through the quarter-wave plate 902, and irradiated on the wafer 1 through the objective lens 10. The irradiated light is reflected or diffracted by the wafer 1, focused by the objective lens 10, and enters the PBS 8 through the quarter-wave plate 902 and the half-wave plate 901. At this time, regarding light reflected or diffracted by the wafer 1, since the zero-order diffracted light and the high-order diffracted light suffer change in polarization by different amounts, respectively, the ratio of PBS transmittance between the zero-order diffracted light and the high-order diffracted light can be altered by rotating the half-wave plate 901 and the quarter-wave plate 902 about the optical axis to the polarization direction of the diffracted light. Details of this unit are disclosed in JP 155099-2000A, which enables implementation of the unit.

FIG. 14 shows an example of a unit for generating polarization differential interference. The unit in FIG. 14 consists of half-wave plates 911, 913, birefringent prisms 912, 914, and a quarter-wave plate 915. Here, each of the birefringent prisms 912, 914 is, for example, a Nomarski-type prism. Next, its operation will be described. The S-polarized illumination light that was emitted from the deformation illumination optical system 7 and transmitted through the PBS 8 enters the half-wave plate 911. At this time, the half-wave plate 911 rotates polarization direction to a direction that makes a certain angle with the optic axis of the birefringent prism 912.

The light transmitted through the birefringent prism 912 is branched into components in two parallel optical paths by the birefringent prism 912, and enters the half-wave plate 913. The half-wave plate 913 rotates the polarization direction to a direction that makes a certain angle to the optic axis of the birefringent prism 914, and enters the light into the birefringent prism 914. Each of the light transmitted through the birefringent prism 914 is branched into components in two parallel optical paths by the birefringent prism 914. Thus, the birefringent prism 914 can generate linearly polarized light beams branched into total four optical paths, that is, two optical paths by the birefringent prism 914 plus two optical paths by the above-mentioned birefringent prism 912. The beams of linearly polarized light in the four optical paths enter the quarter-wave plate 915, each becoming elliptically polarized light, and are irradiated on the wafer 1 through the objective lens 10. A physical phenomenon by the polarization differential interference optical system using a single Nomarski-type prism is the same as that of the common differential interference microscope.

The feature of the polarization differential interference unit of this invention is that by dividing light into four or more light beams, it becomes possible to inspect an orthogonal pattern on the wafer 1. That is, with the normal birefringent prism capable of dividing a single point into two points, the effect of differential interference is achieved only in the direction of a straight line linking the two points. To improve this, this invention enables two-dimensional differential interference by branching the light into optical paths even in the direction making a certain angle with the straight line linking the two points, so that differential interference can be performed regardless of the direction of a circuit pattern.

Incidentally, it is possible to alter a branching direction of the optical path by rotating the birefringent prisms 912, 914 about the optical axis and rotating the polarization direction so that the relation described above is achieved with the half-wave plates 911, 913. By changing the branching direction of the optical path in this way, defects of a circuit pattern in various directions can be inspected with high sensitivity.

Figure 15:
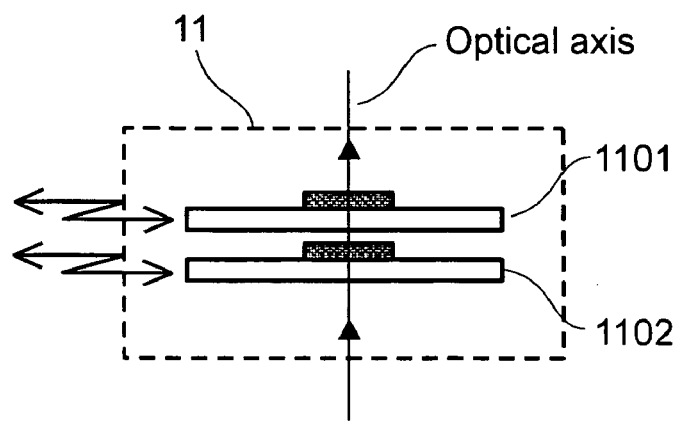
FIG. 15A is a view showing a configuration of a light modulation unit B.
FIG. 15B is a view showing one example of a spatial filter used in the light modulation unit B.
Figure 15:
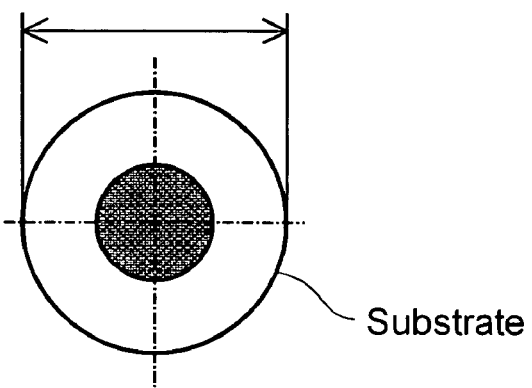
Figure 15:
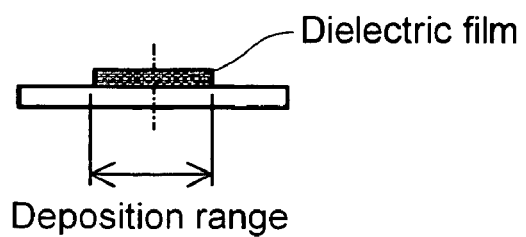
Figure 16:
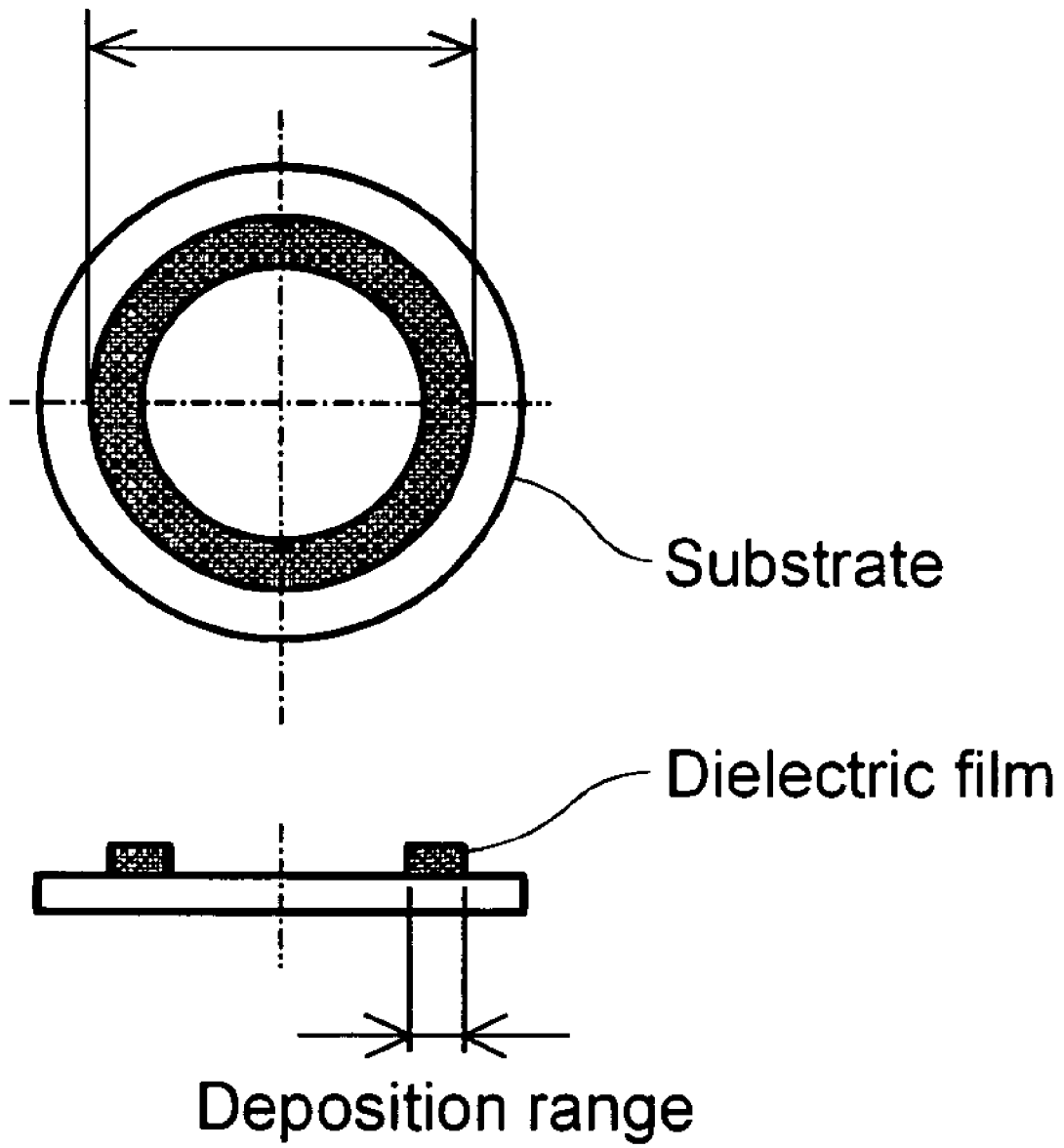
FIG. 16 is a view showing another example of the spatial filter.
Figure 17:
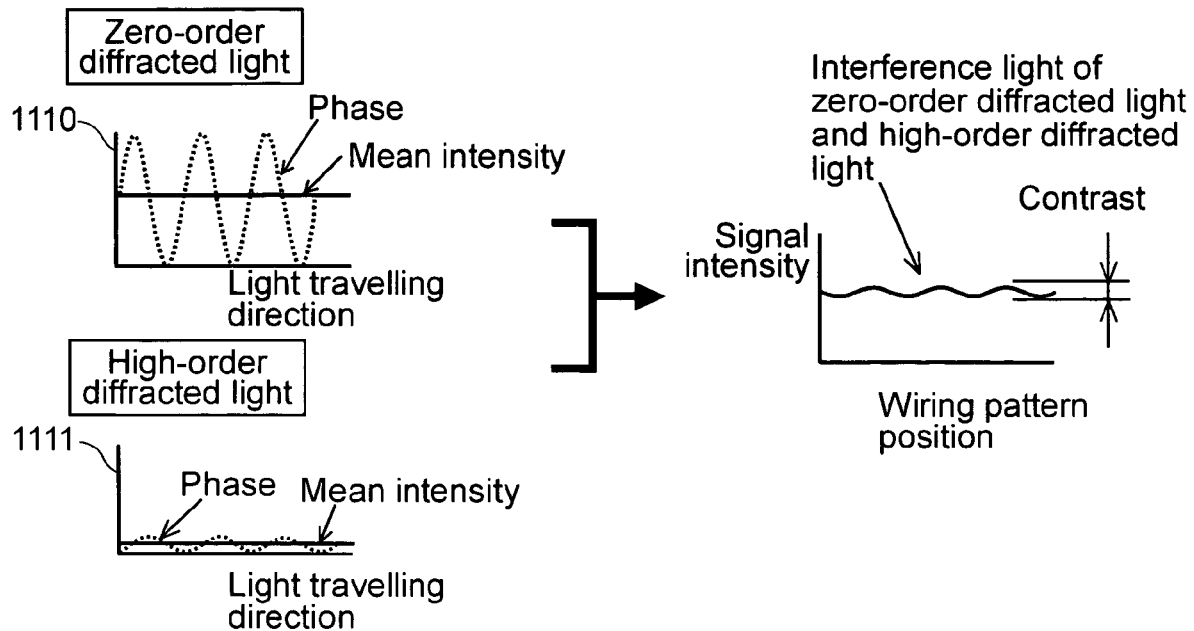
FIG. 17A is a diagram of light intensity when the spatial filter of this invention is not used to show the effect of the spatial filter.
FIG. 17B is a diagram of light intensity when the spatial filter of this invention is used.
Figure 17:
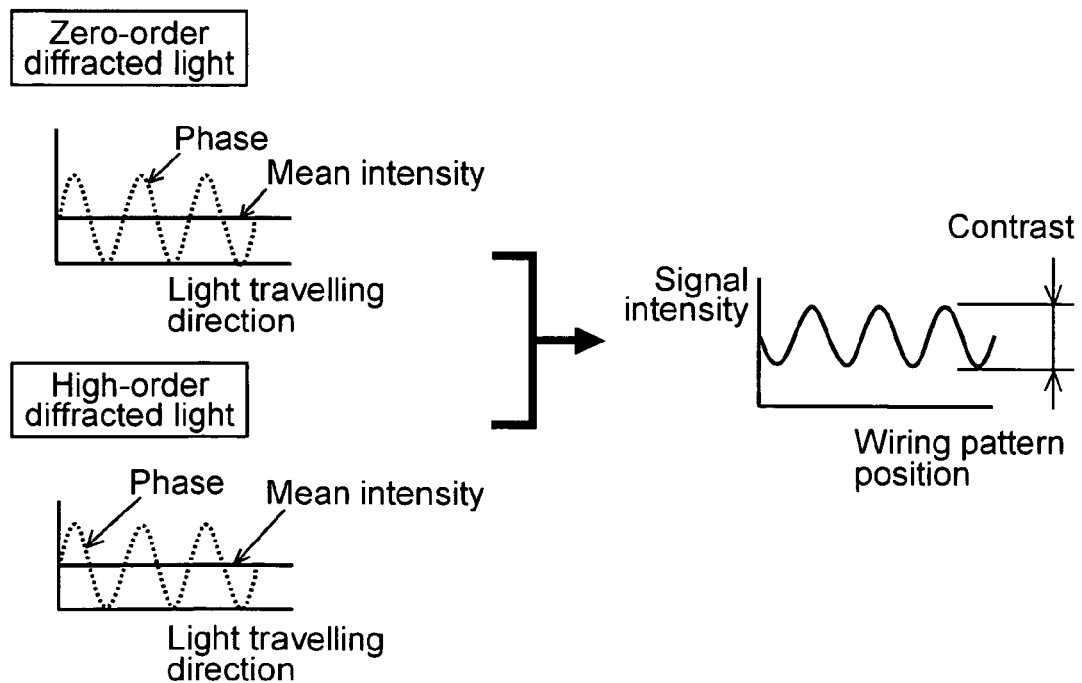

Next, FIGS. 15 through 17 are used to explain details of the light modulation unit B 11. This light modulation unit B 11 is installed in a position that is conjugate with the pupil position of the objective lens 10. The purpose is optical modulation in the pupil position. FIG. 15A is one example of the light modulation unit B 11. The light modulation unit B 11 consists of a spatial filter A 1101 and a spatial filter B 1102. FIG. 15B shows appearances of the spatial filter A 1101 and the spatial filter B 1102. The spatial filter A 1101 is a transparent substrate 1501, such as quartz, on whose central region a dielectric film 1502 is deposited. The dielectric film 1502 is a film designed so that transmitted light in a region with the dielectric film deposited on it and transmitted light in a region with no film deposited on it have a phase difference. The spatial filter B 1102 is a substrate on which a dielectric film is deposited as with the spatial filter A 1101. Further, the spatial filter B 1102 is designed so that the transmitted light in a region with the dielectric film deposited on it and the transmitted light in a region with no film deposited on it have different values of transmittance. Preferably, a deposition range of the dielectric film matches the size of the zero-order diffracted light in the pupil position.

FIG. 16 shows another example of the spatial filter. This is an example of the case where the illumination light irradiated on the wafer 1 is designed to form a ring illumination, and the deposition range of the dielectric film acting as a spatial filter is also made in the form of a circular band. The light modulation unit B 11 has a mechanism of changing a plurality of spatial filters prepared in advance each of which corresponds to a particular shape of the illumination light as shown in FIGS. 15, 16 in conformity to a shape of the illumination light.

FIG. 17 is used to explain the effect of the spatial filter. FIG. 17A shows the light intensity when the spatial filter of this invention is not used. Without the use of the spatial filter, light intensity 1111 of the high-order diffracted light is lower than light intensity 1110 of the zero-order diffracted light; therefore, the zero-order diffracted light causes a large effect on the interference light of the zero-order diffracted light and the zero-order diffracted light, lowering pattern contrast of L&S etc. In contrast to this, since the use of the spatial filter of this invention can lower the intensity of the zero-order diffracted light and increase the intensity of high-order diffracted light relatively, the contrast of the pattern can be increased, as shown in FIG. 17B.

Figure 18:
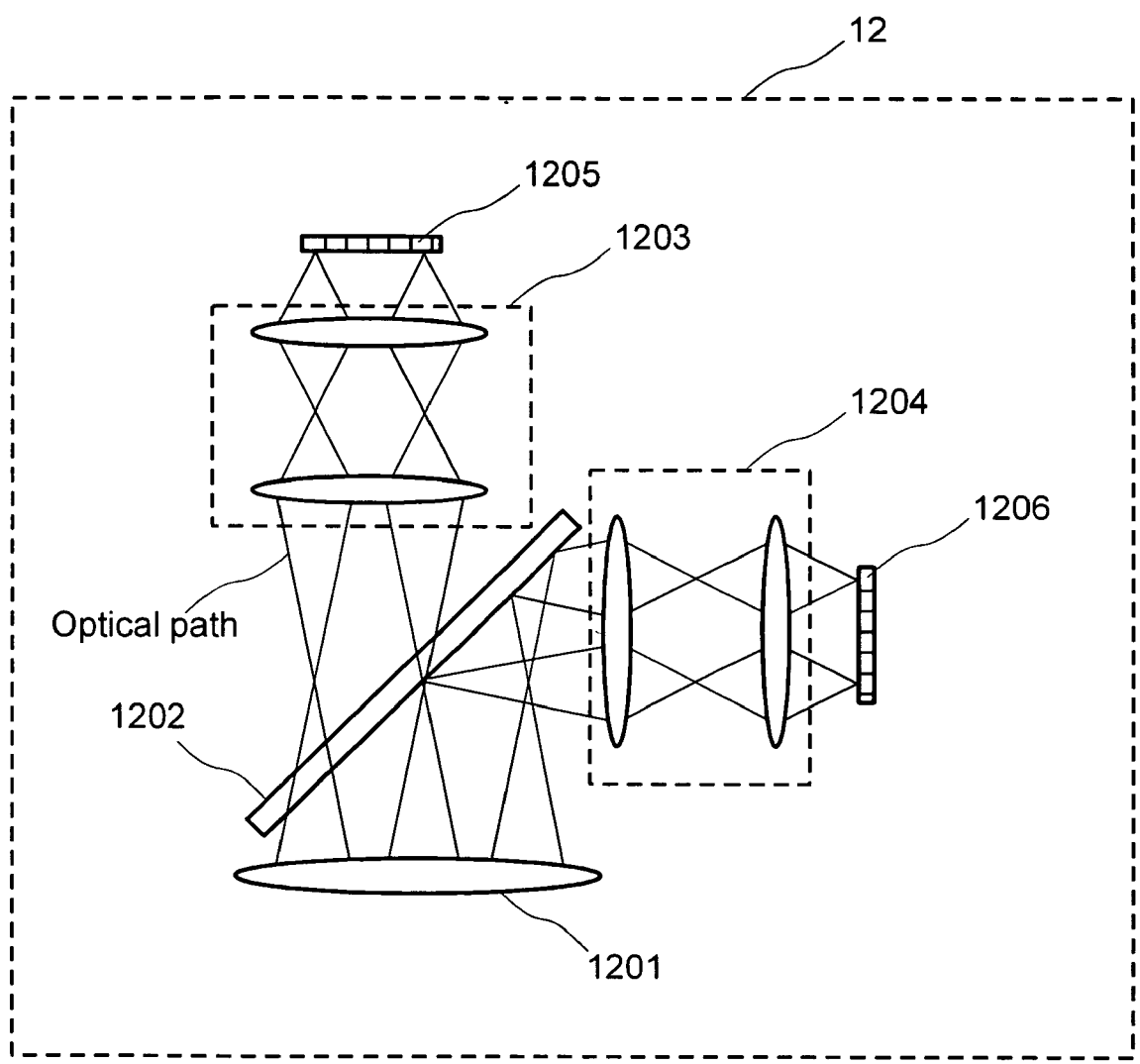
FIG. 18 is a view showing a configuration of a visual-field divided parallel detection part.

Next, details of the visual-field divided parallel detection unit 12 will be described using FIG. 18. The visual-field divided parallel detection unit 12 consists of an imaging lens 1201, a half mirror 1202, relay lenses 1203, 1204, and image sensors 1205, 1206. Its operation will be described. First, the light transmitted through the light modulation unit B 11 described above is focused in a focal position of the imaging lens 1201 by the imaging lens 1201. The focused light is branched into two optical paths by the half mirror 1202 disposed in the focal position; a half area of the detection visual field is made to form an image on the image sensor 1205 through the relay lens 1203, and a remaining half area is made to form an image on the image sensor 1206 through the relay lens 1204. With this configuration, a pattern can be processed in parallel by dividing the detection visual field into two, and consequently processing can be done two times faster than the case where a single image sensor of the same specifications is used, thus enabling high-speed inspection.

Figure 19:
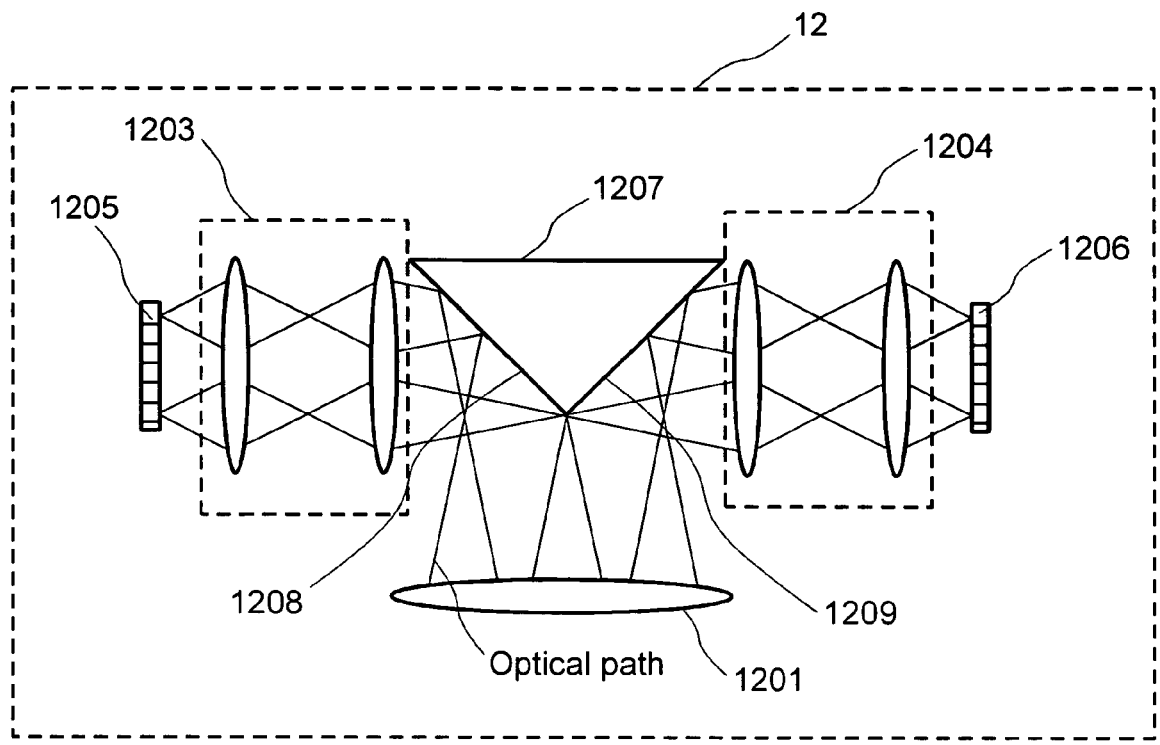
FIG. 19 is a view showing another example of the visual-field divided parallel detection part.

FIG. 19 shows another example of the visual-field divided parallel detection unit 12. This example consists of the imaging lens 1201, a triangular prism 1207, the relay lenses 1203, 1204, and the image sensors 1205, 1206. This example uses the triangular prism 1207 in place of the half mirror 1202 described above. In this example, a half area of the detection visual field is reflected by a reflection plane 1208 of the triangular prism 1207 and is made to form an image on the image sensor 1205 through the relay lens 1203; a remaining half area is reflected by a reflection plane 1209 and is made to form an image on the image sensor 1206 through the relay lens 1204.

Figure 20:
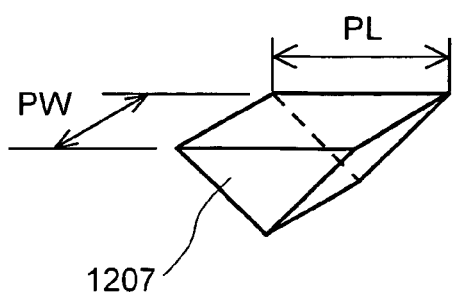
FIG. 20A is a schematic diagram of a triangular prism.
FIG. 20B is a schematic diagram showing a direction of relay lenses and image sensors.
Figure 20:
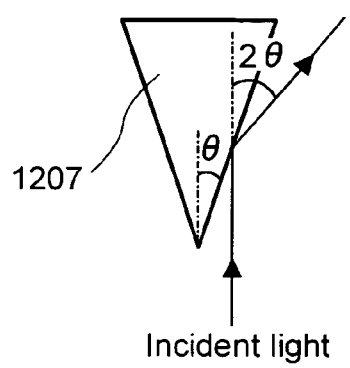

FIG. 20 shows details of the triangular prism 1207. The triangular prism 1207 is in the shape of a triangle pole as shown in FIG. 20A. Here, a base length PL of the triangle must be larger than the width of the formed image in the detection visual field. Moreover, the width PW of the triangle pole must be in such a size that light focused by the imaging lens 1201 does not go out of the reflection planes 1208, 1209. Moreover, the reflection planes 1208, 1209 have reflective surfaces comparable to a mirror. Moreover, representing a half of the vertex angle of the triangular prism 1207 by $\theta$, as shown in FIG. 20B, it is necessary to place the relay lenses 1203, 1204 and the image sensors 1205, 1206 in the direction of angle $2\theta$.

Figure 21:
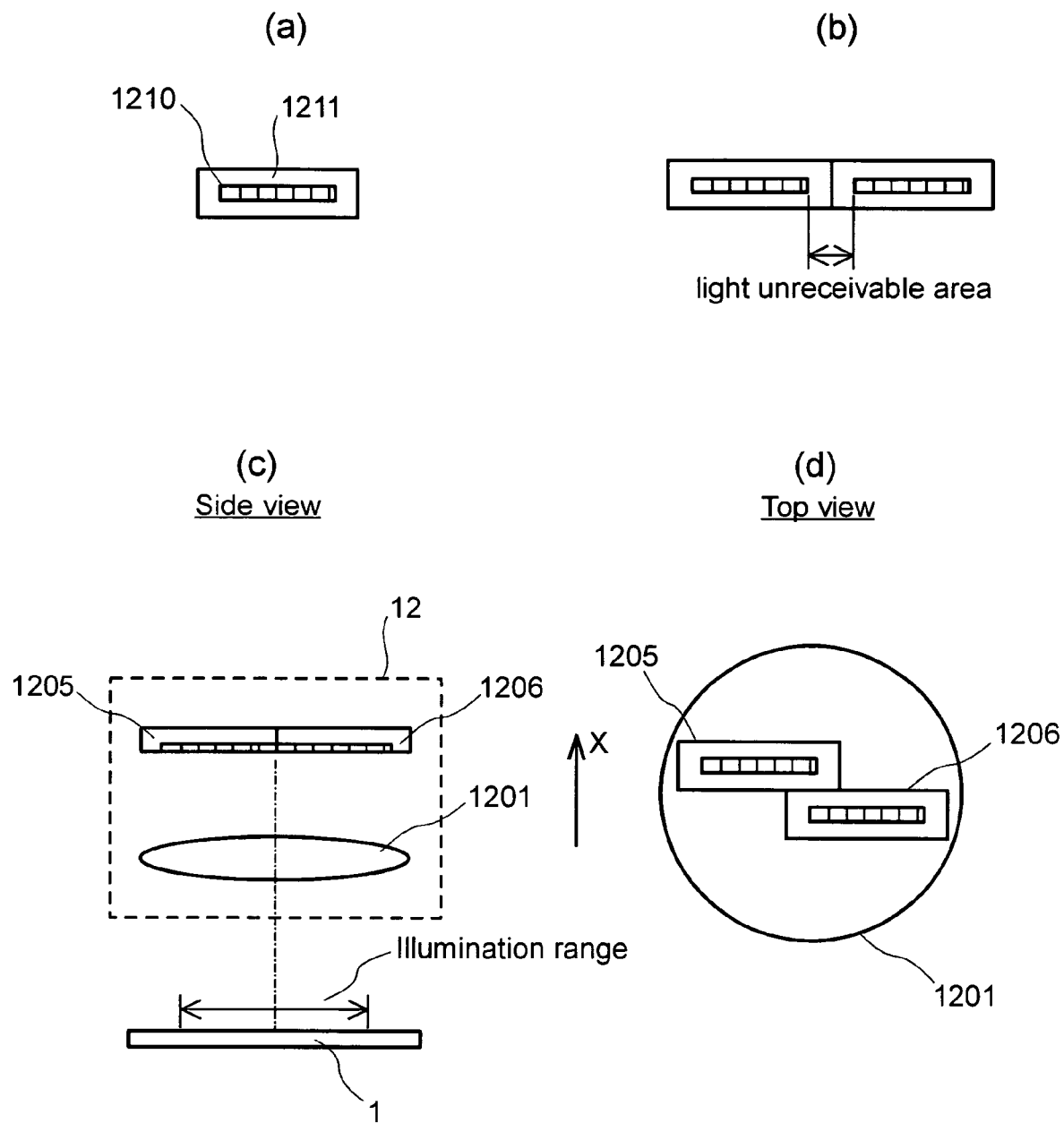
FIG. 21A is a schematic diagram of an image sensor used in another example of the visual-field divided parallel detection part.
FIG. 21B is a schematic diagram of an arrangement of the image sensors.
FIG. 21C is a schematic diagram of another arrangement of the image sensors.
FIG. 21D is schematic diagram of the arrangement of the image sensors of FIG. 21C.

FIG. 21 shows another example of the visual-field divided parallel detection unit 12. This method is a method of arranging image sensors side by side without using the half mirror 1202 and the triangular prism 1207. Since the image sensor consists of a light receiving surface 1210 and a peripheral circuit part 1211, as shown in FIG. 21A, when two or more image sensors are arranged, it is difficult to place the image sensors with their light receiving surfaces close to one another. If they are arranged in series, there occurs a light unreceivable region (a connection of the image sensors 1205, 1206) between the light receiving surfaces, as shown in FIG. 21B. So, in this system, the image sensors are arranged as shown in FIG. 21D so that they are seen as illustrated in FIG. 21C when viewed from its side face, that is, in such a way that the light receiving surfaces of the image sensors are almost continuous. Note that a conveyance stage moves at a constant speed in the X-direction in FIG. 21.

In the foregoing, the three examples were explained, which have respective advantages as follows. In the first method of using the half mirror 1202, a loss in the amount of light occurs by the half mirror, but the configuration is simple. Therefore, the use of this method is recommended when the illumination light source has sufficient output. In the second method of using the triangular prism 1207, since a loss in the amount of light is small, the apparatus can be realized with a low-output-power illumination light source. In the third case of arranging the image sensors side by side, since it does not require the relay lenses 1203, 1204, the apparatus can be made inexpensively. However, it requires a wide illumination area, so the use of this method is recommended when the output of the illumination light source has a margin.

Figure 22:
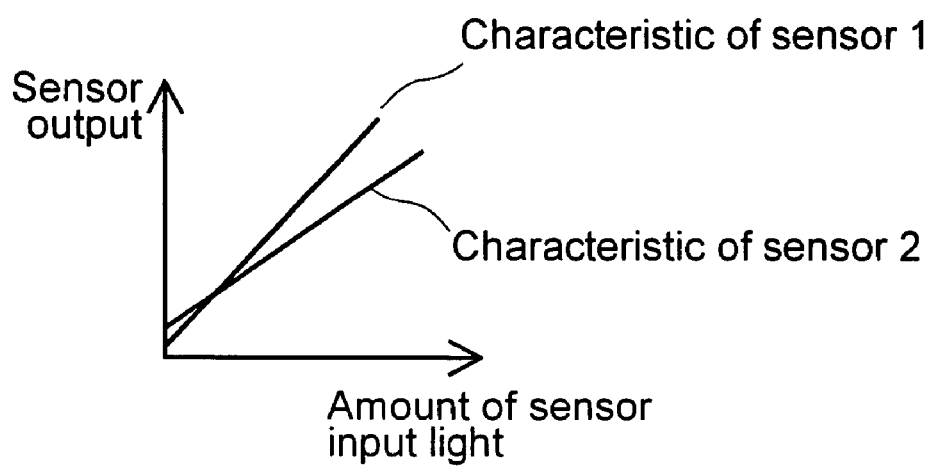
FIG. 22A is a diagram of one example of the I/O characteristics of two image sensors to show output correction of the sensors.
FIG. 22B is a block diagram of output correction of the sensors.
Figure 22:
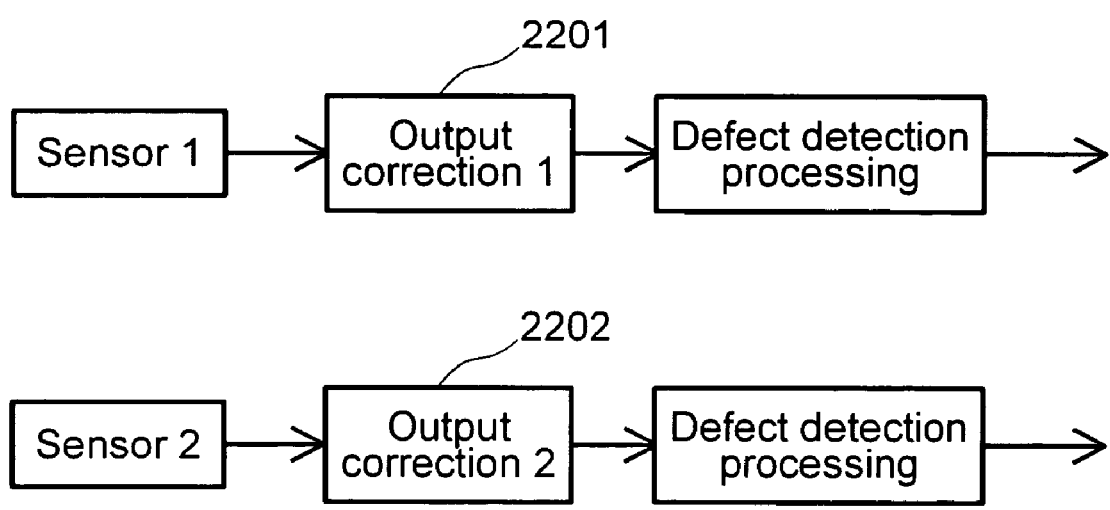

When using two or more image sensors like this embodiment, it is desirable to execute processing to reduce sensitivity unevenness between image sensors. This will be described using FIG. 22. FIG. 22A shows one example of the I/O characteristics of two image sensors. As shown in the figure, an output of the sensor for amount of input light varies at every image sensor because of individual specificity of the image sensor. When such image sensors are used, dispersion of gray-scale value occurs in signal processing of defect detection, and the signals cannot be processed using the same threshold. To solve this problem, this invention features in that a correction circuit for correcting an output of each image sensor is provided as shown in FIG. 22B. For example, assuming that the I/O characteristic of the image sensor 1 is given by Formula 3 and the I/O characteristic of the image sensor 2 is given by Formula 4, these output correction circuits 2201, 2201 make correction as follows: the output of the image sensor 1 is outputted as they were outputted according to the characteristic, and the outputs y2 of the image sensor 2 is subjected to correction of Formula 5.

$$y1 = a1 \times x1 + b1 \quad \text{(Formula 3)}$$

(Here, x1: input, y1: output, and a1 and b1: parameters)

$$y2 = a2 \times x2 + b2 \quad \text{(Formula 4)}$$

(Here, x2: input, y2: output, and a2 and b2: parameters)

$$a1/a2 \times (y2 - b2) + b1 \quad \text{(Formula 5)}$$

In this example, explained is a correction method of the sensor 2 in the case where a relation of the output between the image sensor 1 and the image sensor 2 is a linear relation. In the case where the input-output relation of a sensor is expressed in a high-order polynomial, the correction may be done using a polynomial. Moreover, as long as the relation of the sensor 1 will come close to that of the sensor 2, the output of the sensor 1 may be corrected.

The image sensor described above may be any sensor having sensitivity at the illumination wavelength. For example, a one-dimensional CCD sensor and a TDI image sensor are usable, and photomultipliers aligned in series may be used. Moreover, a two-dimensional CCD sensor, such as a TV camera, may be used.

Figure 23:
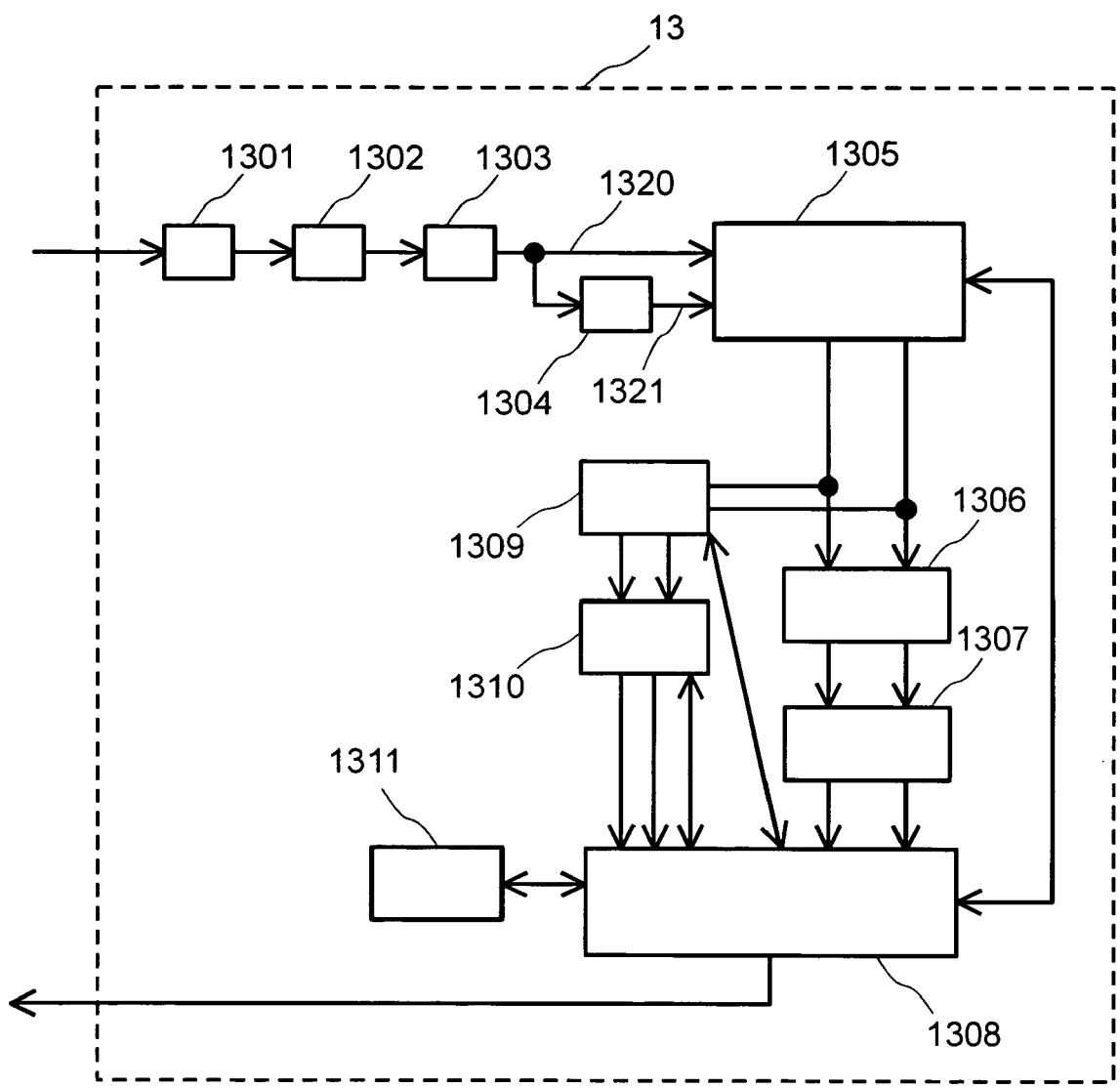
FIG. 23 is a view showing a configuration of a signal processing circuit.

Next, details of the signal processing circuit 13 will be described using FIG. 23. The signal processing circuit 13 consists of an A/D converter 1301, a gray-scale translation unit 1302, an image filter 1303, delay memory 1304, an alignment unit 1305, a local gray-scale translation unit 1306, a comparison processing unit 1307, a CPU 1308, an image input unit 1309, a scatter diagram creation unit 1310, and storing unit 1311.

Its operation is explained as follows. At first, a detected signal obtained in the visual-field divided parallel detection unit 12 is transmitted to the signal processing circuit 13 and is converted to a digital image signal by the A/D converter 1301. Then, the converted digital image signal is transferred to the gray-scale translation unit 1302. The A/D converter 1301 performs A/D conversion of, e.g., 10 bits.

The gray-scale translation unit 1302 performs such gray scale translation as is described in JP No. 320294-1996A on the image signal outputted from the A/D converter 1301. That is, the gray-scale translation unit 1302 corrects an image by logarithmic transformation, exponential transform, polynomial transform, etc. and is configured to output a digital signal of eight bits etc.

The image filter 1303 is a filter for rejecting efficiently image noises peculiar to the illumination light from the image signal whose gray scale was translated.

The delay memory 1304 is a storage unit for storing the image signal including one cell that constitutes a semiconductor wafer, or several cells, or one die, or several dies outputted from the image filter 1303. The delay memory 1304 delays the output signal comparing to the image signal from the image filter 1303.

The alignment unit 1305 is a unit that detects the amount of displacement between the detected image signal 1320 outputted from the image filter 1303 and the delayed image signal 1321 outputted from the delay memory 1304 using the normalized correlation technique and performs pixel-by-pixel alignment.

The local gray-scale translation unit 1306 is a unit that translates the gray scale for the both or one of the image signals so that signals having different feature quantities (brightness, a differential value, standard deviation, texture, etc.) will coincide in these feature quantities.

The comparison processing unit 1307 is a unit that detects defects based on differences of the feature quantities by comparing the image signals each of which is subjected to gray-scale translation in the local gray-scale translation unit 1306.

By having inputted the coordinates of array data etc. on the wafer 1 from the I/O unit 14 in advance, the CPU 1308 creates defect inspection data based on the coordinates of the array data etc. on the wafer 1 and stores it in the storing unit 1311. The defect inspection data is transmitted to the I/O unit 14 as needed. Details of the comparison processing unit 1307 may be as they are disclosed in JP No. 212708-1986A. For example, it consists of an image aligning circuit, a differential image detecting circuit for detecting a differential image of aligned images, a circuit for detecting inconsistency of images by binarizing the differential image, and a feature extracting circuit for calculating areas, lengths (projected lengths), coordinates, etc. from the binarized output.

The image input unit 1309 is a unit to which an image is inputted synchronously or asynchronously in order to create a scatter diagram of images that were aligned, pixel by pixel, in the alignment unit 1305. The scatter diagram creation unit 1310 has a function of creating the scatter diagram of feature quantities of the detected image and the reference image, which will be displayed in the I/O unit 14 etc., for the both images inputted into the image input unit 1309.

Figure 24:
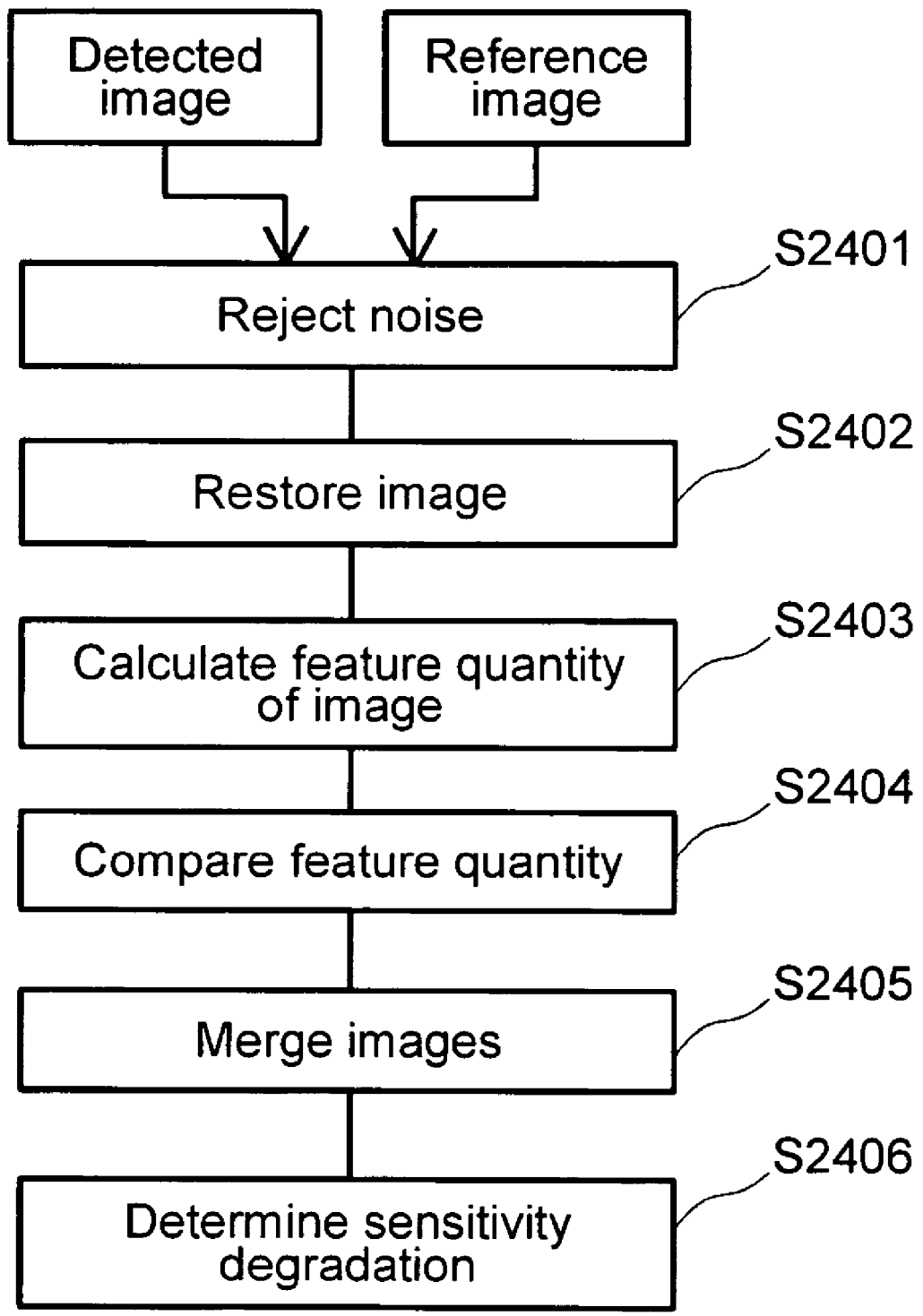
FIG. 24 is a flowchart showing a flow of signal processing.

FIG. 24 shows one example of a sequence in the signal processing circuit 13. First, the detected image and the reference image that were inputted are subjected to noise rejection processing Step 2401 as needed to improve S/N of the images. For noise rejection, various filters are prepared and can be selected according to an object and the quality of a noise. For example, there is a method in which values of neighboring pixels of a target pixel are used with weights assigned thereto. Actual processing is that values of M×N neighboring pixels of the target pixel are multiplied with filter coefficients and added to the value of the target pixel.

Figure 25:
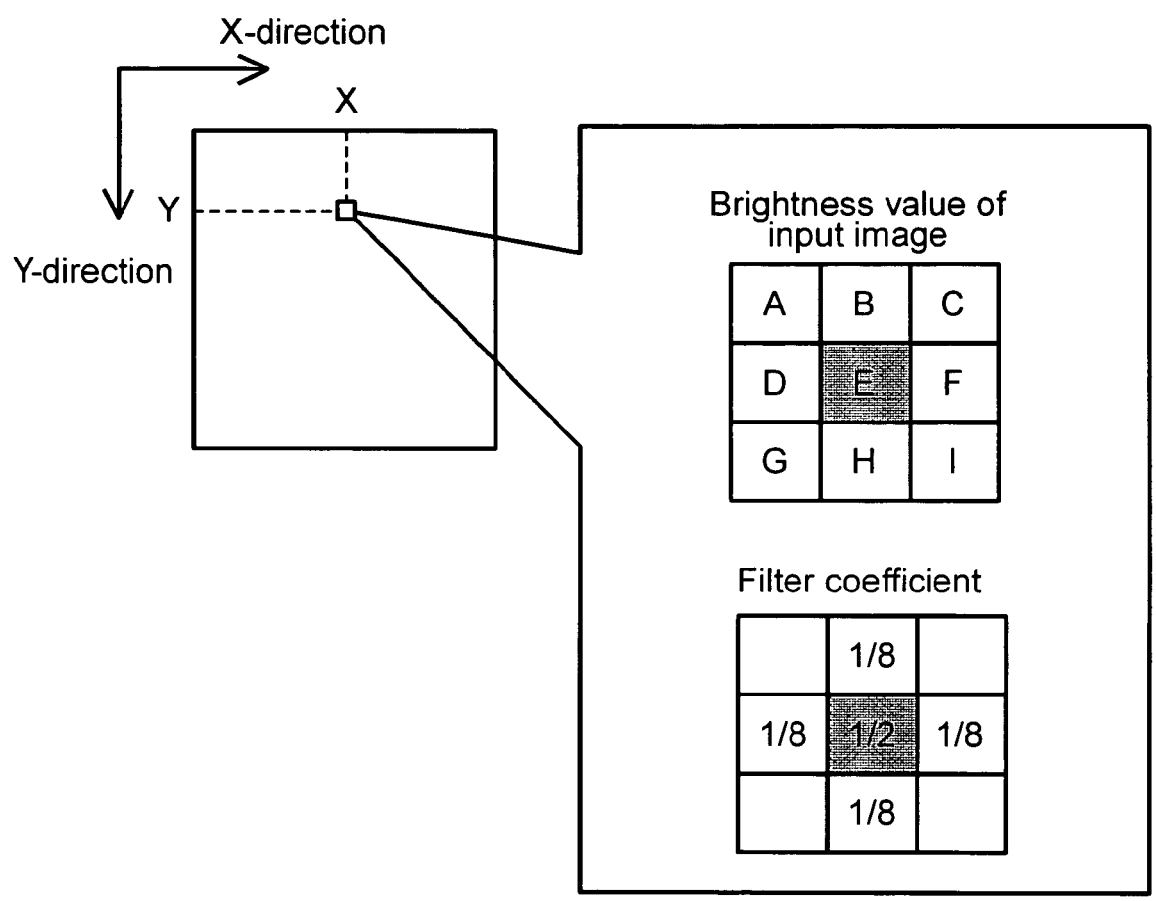
FIG. 25 is a view showing an image processing filter.

FIG. 25 shows one example of the noise-rejection filter. Shown in FIG. 25 is the case where M and N are set as M=N=3 and the weight of each neighboring pixel value is ⅛. A value F (x, y) of the target pixel is expressed by Formula 6.

$$F(x, y) = B \times \tfrac{1}{8} + D \times \tfrac{1}{8} + F \times \tfrac{1}{8} + H \times \tfrac{1}{8} + E \times \tfrac{1}{8} \quad \text{(Formula 6)}$$

The size of a filter and coefficients can be flexibly changed using a look-up table.

There is a median filter as another example of the noise-rejection filter. This is a filter of taking a median of brightness values of neighboring pixels specified, and can reject an effect of a singular point. Further another example is a method of using a Gaussian function. This is a filter of smoothing an image by convoluting the input image f (x, y) with a two-dimensional Gaussian function of a mean: 0 and a variance: $\sigma^2$ (Formula 7) according to Formula 8.

$$(x, y) = (1/2 \times \pi \times \sigma^2) \cdot \exp(-(x^2 + y^2)/2/\sigma^2) \quad \text{Formula 7}$$

$$F(x, y) = G(x, y) \otimes f(x, y) \quad \text{Formula 8}$$
$$= \int\int G(x+u, y+v) \cdot f(x, y) du dv$$

Moreover, as another example, it is possible to use Fourier transform to reject noises that occur regularly.

Next, restoration processing Step 2402 of an image that was degraded by noise rejection is executed. For example, this includes restoration processing by the Wiener filter. This is one that provides an image such that a mean square error between an input image f (x, y) and an image f' (x, y) after restoration becomes the minimum.

Further, whether there is a large difference in the appearance between a detected image and a reference image that are to be compared is checked. Evaluation indexes include contrast, dispersion of brightness (standard deviation), frequencies of noise components, etc. If a large difference in the evaluation indexes exist between the images, processing to calculate the feature quantities Step 2403 and processing to compare calculated feature quantities are executed, and then merge processing to merge images Step 2405 is executed. If a feature quantity is in such a level that the feature quantity cannot be merged, sensitivity is lowered in the comparison processing unit 1307 so that generation of a false report is suppressed. After that, processing Step 2406 to determine sensitivity lowering is executed. A detailed method for detecting defects in the signal processing circuit 13 is disclosed in JP 194323-2001A, which can realize the method.

Next, the I/O unit 14 will be described. The I/O unit 14 is an interface unit with the user and is also an input-output circuit of data and control signals. Here, input information from the user includes, for example, layout information and a name of a wafer to be inspected, inspection conditions, etc. of the optical system described above. Output information to the user includes, for example, defect inspection results, images of detected defects, etc.

Embodiment 2

Figure 26:
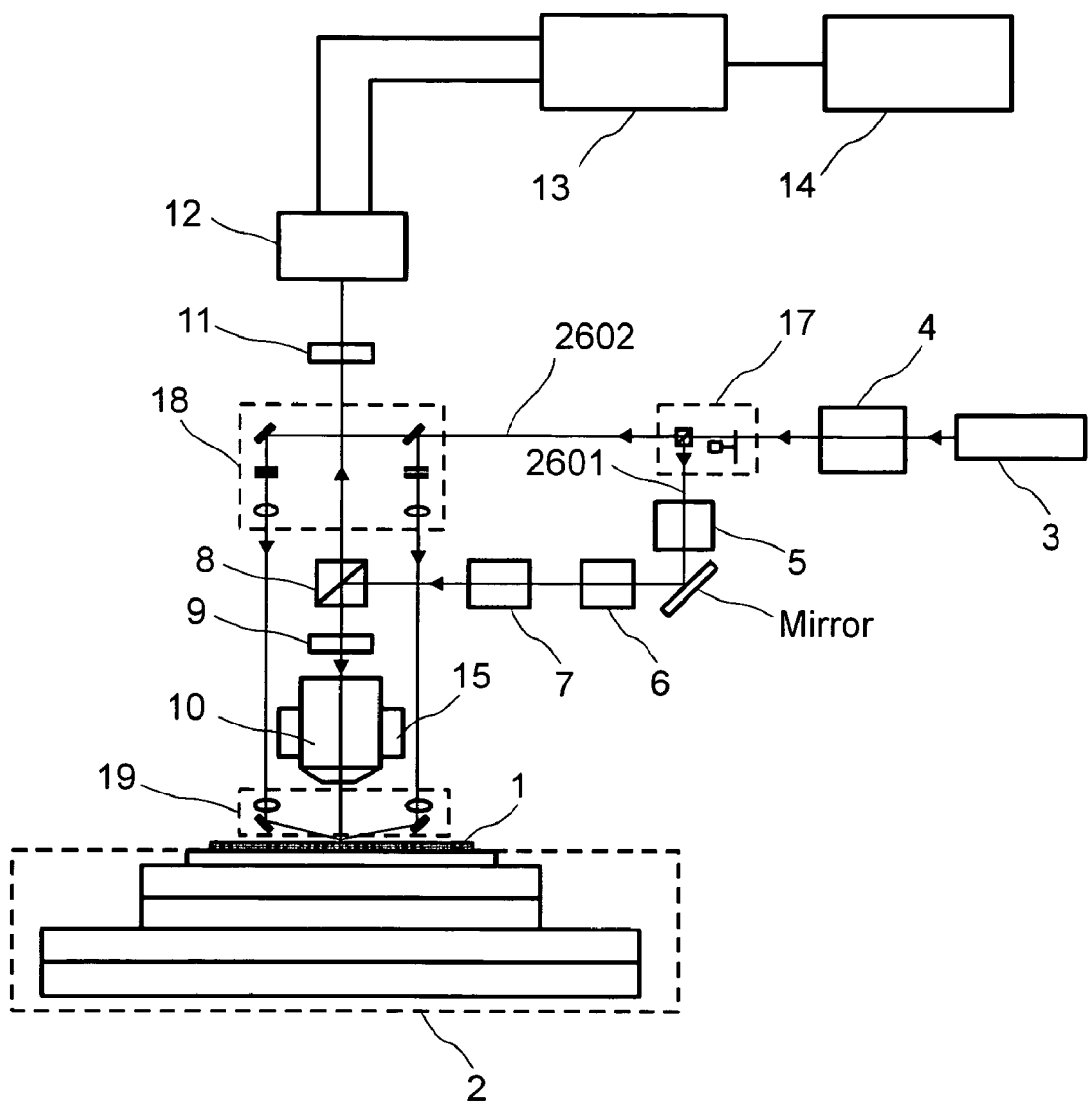
FIG. 26 is a block diagram showing another embodiment of this invention.

Another embodiment of a pattern-defect inspection apparatus according to this invention is shown in FIG. 26. The pattern-defect inspection apparatus of this embodiment consists of: the conveyance system 2 for placing and moving the wafer 1 to be inspected, the illumination light source 3, the pseudo continuous-wave forming optical system 4, the beam formation optical system 5, the coherence reduction optical system 6, the deformation illumination optical system 7, the PBS 8, the light modulation unit A 9, the objective lens 10, the light modulation unit B 11, the visual-field divided parallel detection unit 12, the signal processing circuit 13, the I/O unit 14, the A/F unit 15, a polarized-light dark-field illumination optical system A 18, a polarized-light dark-field illumination optical system B 19, and controllers, relay lenses, and mirrors of the units not shown in the figure.

Next, its operation will be described. The illumination light emitted from the illumination light source 3 enters the pseudo continuous-wave forming optical system 4, where its amount of light is averaged or almost equalized temporally. This illumination light emitted from the pseudo continuous-wave forming optical system 4 enters an optical-path branching optical system 17, and is branched into optical paths in two directions. As in the case of the embodiment 1, the illumination light that was branched into an optical path 2601 of the optical paths in the two directions enters the beam formation optical system 5, where its beam diameter and illuminance distribution adjusted. This illumination light emitted from the beam formation optical system 5 enters the coherence reduction optical system 6, where its temporal and spatial coherence is reduced, and the illumination light emitted from the coherence reduction optical system 6 is made to change its illuminance distribution in the pupil position of the objective lens 10 by the deformation illumination optical system 7. The S-polarization component of the illumination light emitted from the deformation illumination optical system 7 is reflected to the objective lens 10 side by the PBS 8, and is irradiated on the wafer 1 through the light modulation unit A 9 and the objective lens 10. Hereafter, the illumination light irradiated in this particular optical path, namely, the illumination light irradiated through the objective lens 10, is called the bright field illumination.

On the other hand, the illumination light that was branched into an optical path 2602 by the optical-path branching optical system 17 enters the polarized-light dark-field illumination optical system A 18, is subjected to optical path branching and polarization control, and irradiated on the wafer 1 through the polarized-light dark-field illumination optical system B 19. Hereafter, the illumination light irradiated in this particular optical path, namely, the illumination light irradiated without passing through the objective lens 10, is called the dark field illumination.

The light irradiated on the wafer 1 as the bright field illumination and as the dark field illumination is diffracted by the wafer 1, focused by the objective lens 10, and enters the PBS 8 through the light modulation unit A 9. The P-polarization component of the incident light is transmitted through the PBS 8, and forms an image on an image sensor in the visual-field divided parallel detection unit 12 through the light modulation unit B 11. The image sensor converts it to an image signal. The image signal thus converted is subjected to defect detection processing in the signal processing circuit 13, which detects defects on the wafer 1. By making the conveyance system 2 move the wafer 1, the above processing is executed on the whole surface of the wafer 1, and inspection results are displayed in the I/O unit 14. This I/O unit 14 has an interface function of receiving input information from the user, and enables transmission and reception of control signals between the I/O unit and the controllers. In addition, the A/F unit 15 emits a signal for moving the wafer 1 to the focal position of the objective lens 10, and controls the conveyance system 2 with the controller to move the wafer 1 in real time.

Figure 27:
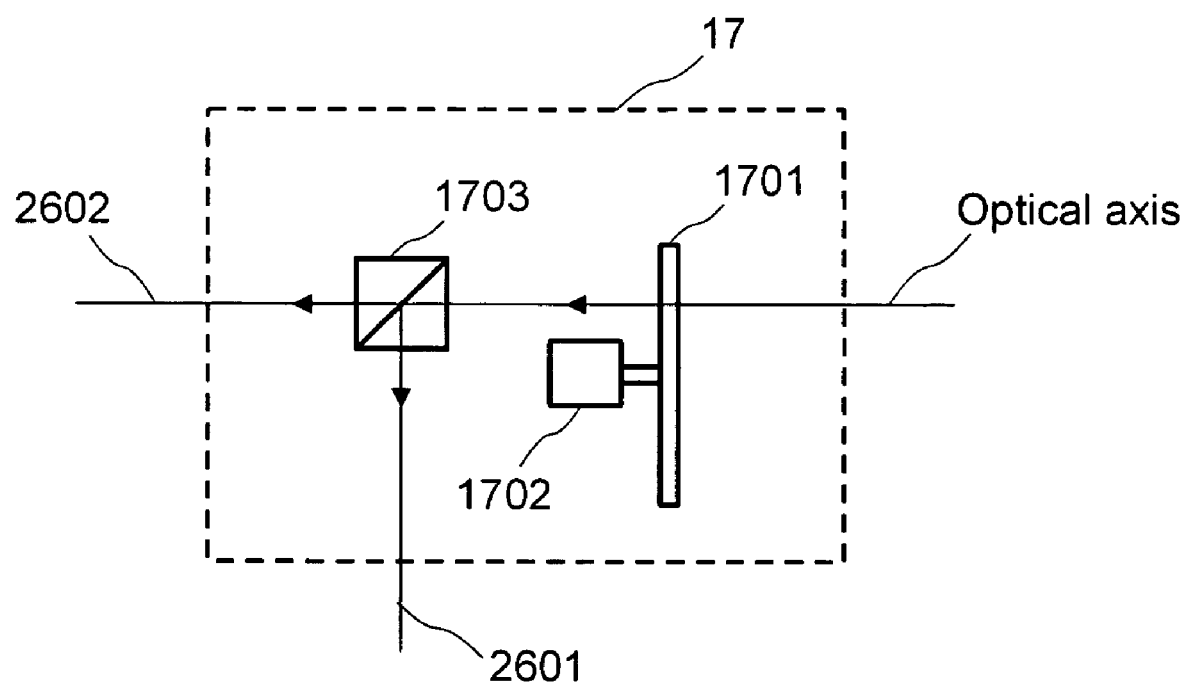
FIG. 27 is a view showing a configuration of an optical-path branching optical system.

Details of the optical-path branching optical system 17 will be described using FIG. 27. The optical-path branching optical system 17 consists of a half-wave plate 1701, a rotating motor 1702, and a PBS 1703. The light emitted from the pseudo continuous-wave forming optical system 4 enters the optical-path branching optical system 17 as linearly polarized light. In the optical-path branching optical system 17, first, the polarization direction of the light is rotated by the half-wave plate 1701 and the polarized light thus rotated is branched into the optical path 2601 and the optical path 2602 by the PBS 1703. In the PBS 1703, the S-polarization component of the polarized light thus rotated is reflected to the optical path 2601 side, and the P-polarization component is transmitted to the optical path 2602 side.

The amounts of light branched into the optical path 2601 and the optical path 2602 can be adjusted by an angle of rotation of the half-wave plate 1701. For example, when the light transmitted through the half-wave plate 1701 is the S-polarized light, the whole light emitted from the illumination light source 3 will be irradiated as the bright field illumination, and when the light transmitted through the half-wave plate 1701 is the P-polarized light, the whole light emitted from the illumination light source 3 will be irradiated as the dark field illumination. If the light is light that has the amounts of S-polarized light and P-polarized light at a ratio of 1:1, the wafer 1 is irradiated by the bright field illumination and the dark field illumination whose intensities make a ratio of 1:1, performing bright and dark field illumination. Here, adjustment of rotational angle of the polarization direction by the half-wave plate 1701 may be done by the rotating motor 1702. Moreover, regarding the amount of adjustment, it is recommended to change it depending on the surface conditions of a wafer to be inspected. For example, in a step in which a metal film, such as of Al, is exposed on the uppermost surface, it is better to increase a component of the dark field illumination.

Figure 28:
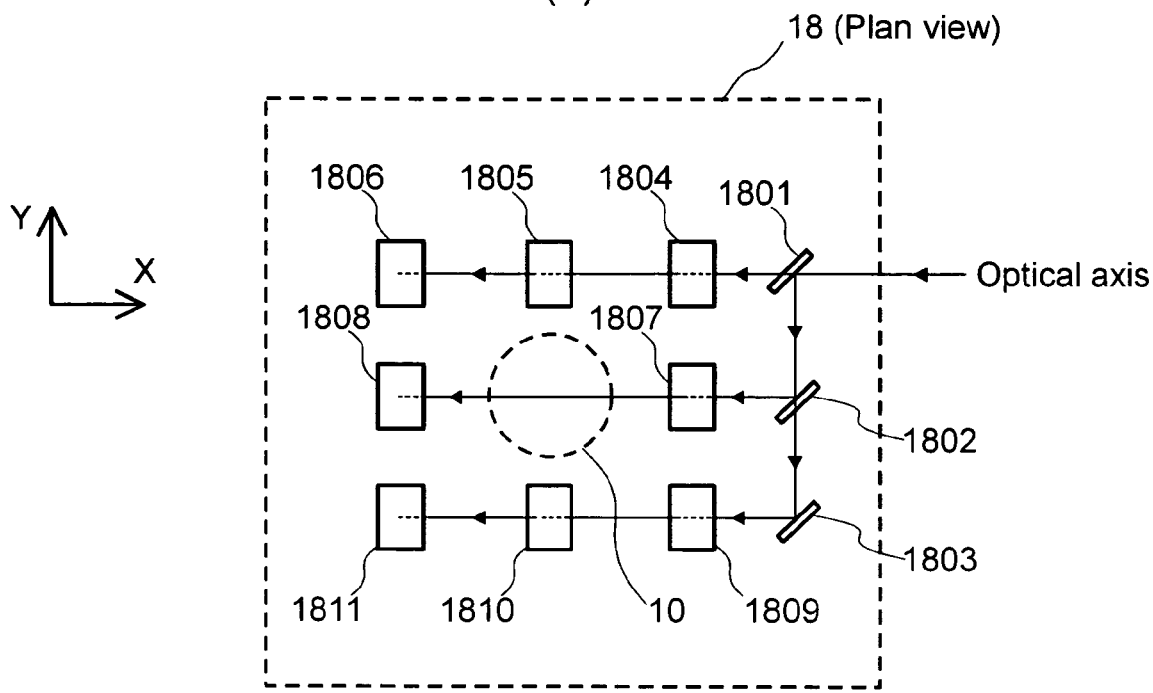
FIG. 28A is a plan view of a polarized-light dark-field illumination optical system A to show a configuration thereof.
FIG. 28B is a front view of the polarized-light dark-field illumination optical system A.
Figure 28:
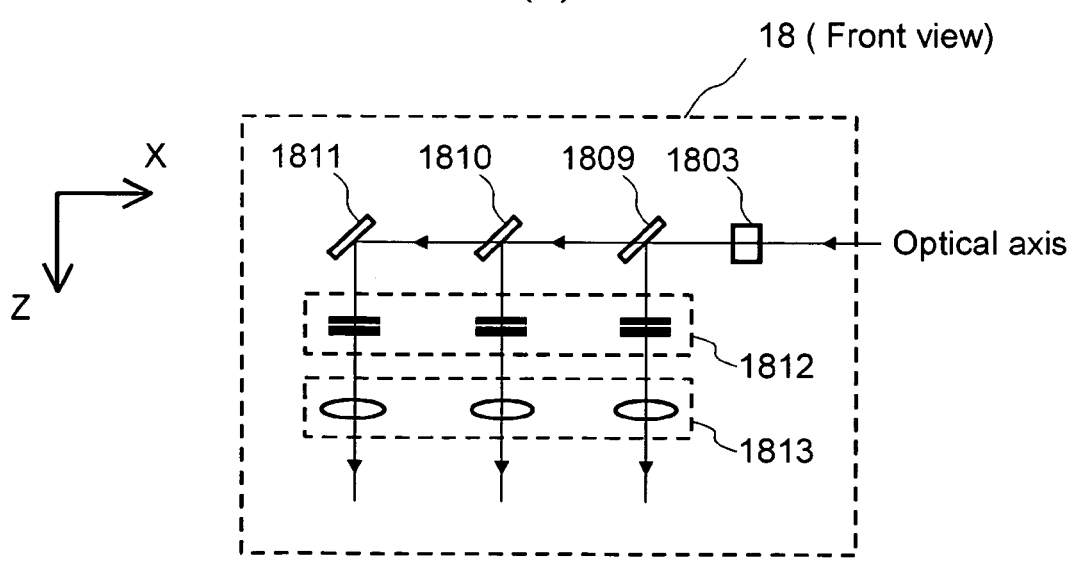

Details of the polarized-light dark-field illumination optical system A 18 will be described using FIG. 28. FIG. 28A is a plan view of the polarized-light dark-field illumination optical system A 18, and FIG. 28B is a front view thereof. The polarized-light dark-field illumination optical system A 18 consists of partial mirrors 1801, 1802, 1804, 1805, 1807, 1809, and 1810, total reflection mirrors 1803, 1806, 1808, and 1811, a polarization control unit 1812, and relay lenses 1813.

Next, its operation will be described. Light incident on the polarized-light dark-field illumination optical system A 18 is branched into two optical paths in two directions by the partial mirror 1801. The light transmitted through the partial mirror 1801 is further reflected in the direction of the Z-axis by partial mirrors 1804, 1805 and the total reflection mirror 1806, the amounts of the reflected light being dependent on their reflectance values. On the other hand, light reflected by the partial mirror 1801 is branched into two optical paths so as to have the amounts of light depending on the transmittance and reflectance of the partial mirror 1802 and the total reflection mirror 1803, and further reflected in the direction of the Z-axis by the partial mirrors 1807, 1809, and 1810 and the total reflection mirror 1808, 1811, the amounts of the reflected light being dependent on their reflectance values. The beams of the reflected light in the direction of the Z-axis are controlled to have specific polarization states by the polarization control unit 1812. The polarization control unit 1812 consists of half-wave plates and quarter-wave plates. The light transmitted through the polarization control unit 1812 is emitted through the relay lenses 1813.

Here, the mirrors 1804, 1805, 1806, 1807, 1808, 1809, 1810, and 1811 are arranged so that the reflected light in the direction of the Z-axis passes along the outside of the objective lens 10.

Figure 29:
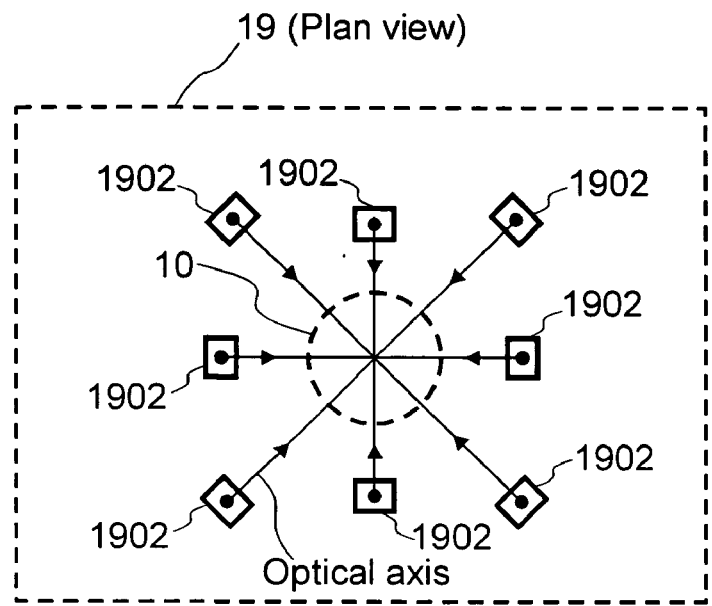
FIG. 29A is a plan view of a polarized-light dark-field illumination optical system B to show a configuration thereof.
FIG. 29B is a front view of a polarized-light dark-field illumination optical system B.
Figure 29:
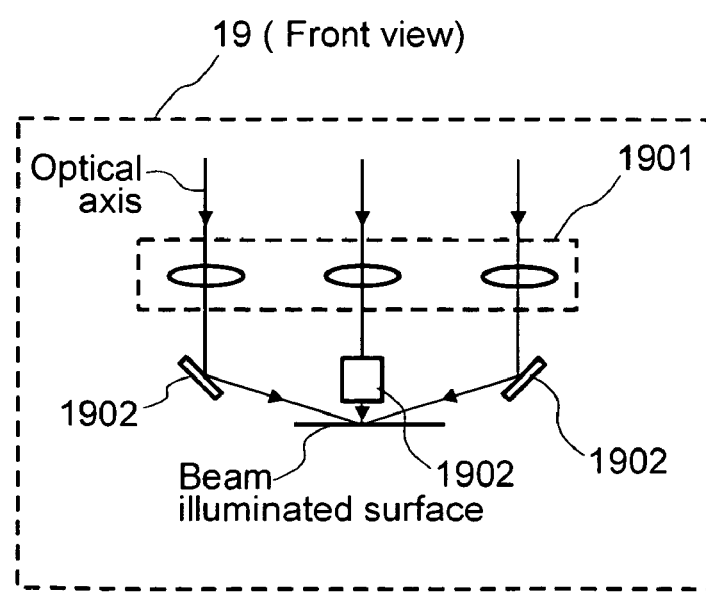

Next, details of the polarized-light dark-field illumination optical system B 19 will be described using FIG. 29. FIG. 29A is a plan view of the polarized-light dark-field illumination optical system B 19, and FIG. 29B is a front view thereof. The polarized-light dark-field illumination optical system B 19 consists of a relay lens 1901 and a total reflection mirror 1902. The illumination light emitted from the polarized-light dark-field illumination optical system A 18 described above is transmitted through the relay lens 1901 disposed downstream of the relay lens 1813 of the polarized-light dark-field illumination optical system A 18, and reflected toward the focal position of the objective lens 10 by the total reflection mirror 1902.

Figure 30:
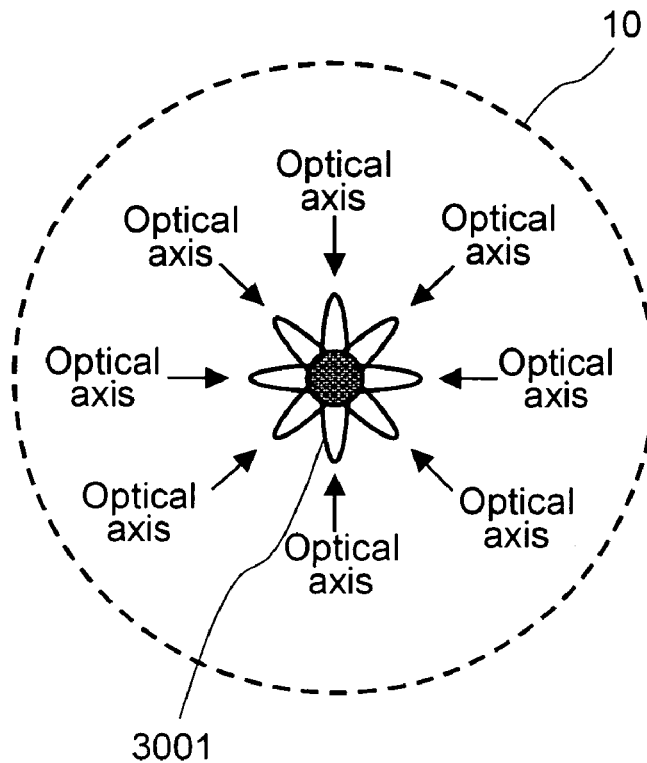
FIG. 30 is a diagram showing an illumination range of the dark field illumination.
Figure 31:
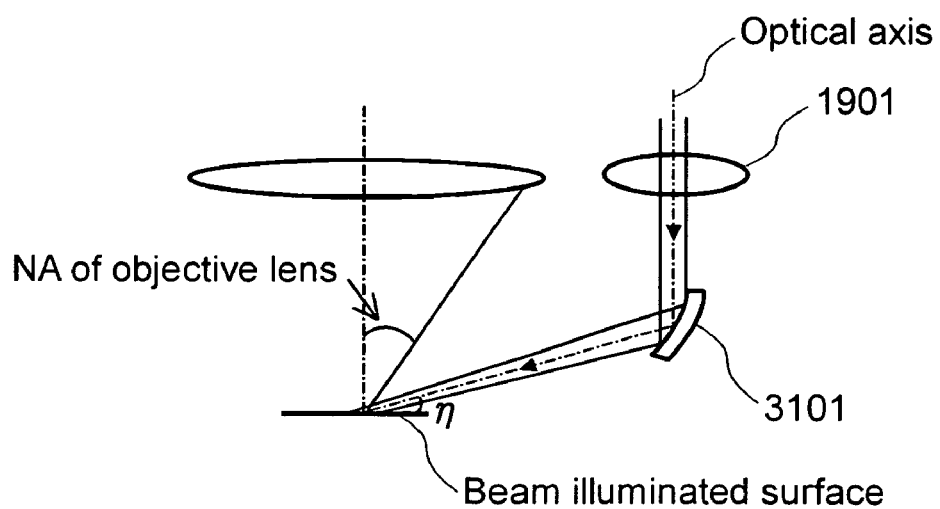
FIG. 31 is a view showing an example of irradiation by a parabolic mirror.

FIG. 30 shows a state of the reflected light. The beams of the reflected light are incident toward a lens center of the objective lens 10 from several directions, and overlap in an illumination range 3001 needed to be illuminated. Note that, in this example, an illuminating method using the total reflection mirror 1902 was described, but a parabolic mirror 3101 may be used to collect the light, as shown in FIG. 31. Although the total reflection mirror 1902 system enables the use of low-price optical components, the illuminance efficiency is lowered and hence it is good to adopt it in the case where the amount of illumination light is sufficient. It is good to use the parabolic mirror 3101 system in the case where the illumination light is intended to be irradiated efficiently. Moreover, for the illumination angle η, an angle in which the illumination light is irradiated from the outside the NA range of the objective lens 10 is recommended, and a range of 1 to 20 degrees from the wafer surface is desirable.

Note that this embodiment was explained in the example where the dark field illumination with eight beams is performed. However, the eight beams are not necessarily required; with one or more beams, the effect of the dark field illumination can be achieved. The eight beams of the illumination light explained in this example can be chosen in terms of irradiation direction and the number of beams in the dark field illumination by blocking any of the beams with shutters not shown in the figure. Although in this embodiment one light source is branched into optical paths and one of them is used to perform the dark field illumination, it is not necessarily to branch a single light source to use two beams and another light source may be used instead for the dark field illumination. If another light source is used, the illumination light source for the bright field illumination can be reduced to low output power. Therefore, the life of the illumination light source can be prolonged and an apparatus of a low running cost can be expected. Moreover, there is an advantage that the optical-path branching optical system 17 becomes unnecessary and the optical components can be decreased in number. Furthermore, a part of the dark field illumination may be used as illumination for A/F instead of setting up the A/F unit 15.

By simultaneous irradiation of the dark field illumination and the bright field illumination that were explained in the above, the amount of detected light from grain that may occur in Al wiring etc. can be stabilized, and hence pseudo defects arising from the grain can be decreased.

Figure 32:
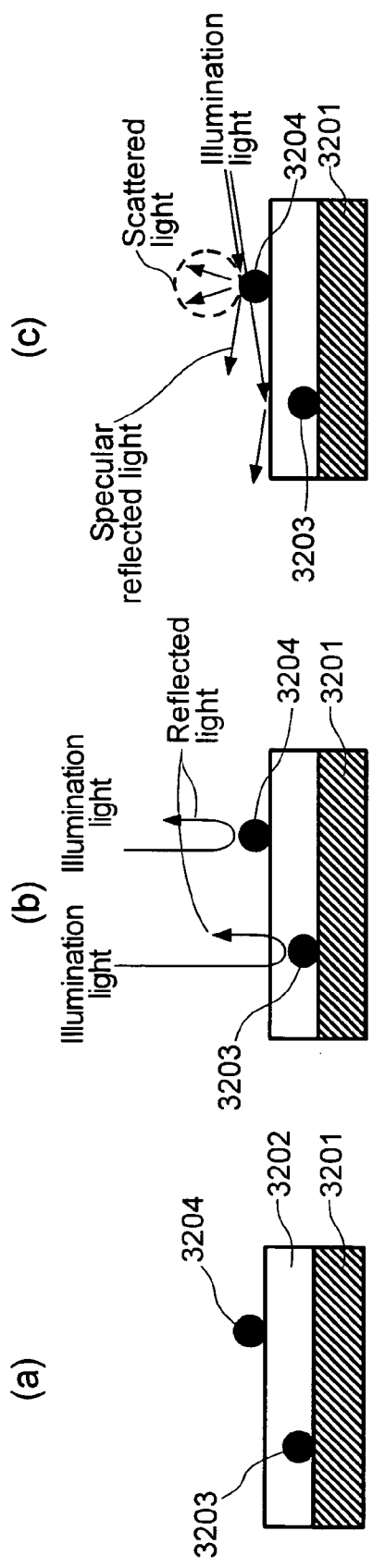
FIG. 32A is a schematic diagram of a structured object to show the principle of defect classification.
FIG. 32B is a schematic diagram of the structured object irradiated with the bright field illumination.
FIG. 32C is a schematic diagram of the structured object irradiated with the dark field illumination.

Next, a method for classifying defects using the dark field illumination will be described. A principle will be explained using FIG. 32. FIG. 32A is a view showing a candidate to be separated from defects. FIG. 32A shows a part of the cross section of an LSI. In this example, on an opaque material 3201 (metal film etc.) at the illumination wavelength of the illumination light source 3, a transparent material 3202 (insulator film etc.) at the illumination wavelength is deposited. A defect 3203 exists in the film of the transparent material 3202, and a defect 3204 exists on the upper side of the transparent material 3202 together with defect 3203.

When the bright field illumination is irradiated on a structured object as shown in FIG. 32A, reflected light from the both defects 3203, 3204 will be detected, as shown in FIG. 32B, and they will be detected as defects, respectively. On the other hand, when the dark field illumination is performed, the illumination light is reflected on the surface of the transparent material 3202, as shown in FIG. 32C, for a physical reason, such as the Brewster angle etc., and does not reach the defect 3203, and hence the detected light from the defect 3203 cannot be obtained, while the illumination light can reach the defect 3204 above the transparent material 3202, and hence scattered light from the defect 3204 will be obtained (but, specular reflected light will not be obtained). Therefore, by comparing detected defect coordinates with the bright field illumination and detected defect coordinates with the dark field-illumination, it becomes possible to classify whether it is in the film of the transparent material 3202 or on the film.

Figure 33:
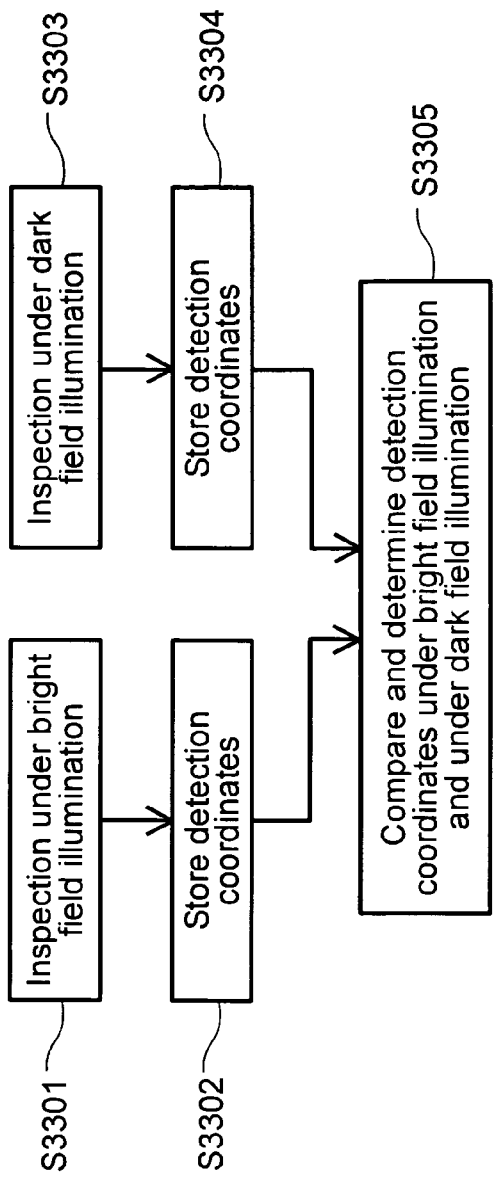
FIG. 33 is a flowchart showing a sequence of defect classification.

FIG. 33 shows a sequence. First, inspection is performed with the bright field illumination (Step 3301), and the detection coordinates are stored (Step 3302). Next, inspection is performed with the dark field illumination (Step 3303), and the detection coordinates are stored (Step 3304). Next, the detection coordinates with the bright field illumination are compared with the detection coordinates with the dark field illumination. When the both coordinates agree, it is determined as a defect on the film; when not in agreement, it is determined as a defect in the film (Step 3305). Note that since any defect detected only with the dark field illumination is considered as a defect on the film according to the principle described above, it is appropriate to determine it as a defect on the film.

Embodiment 3

Figure 34:
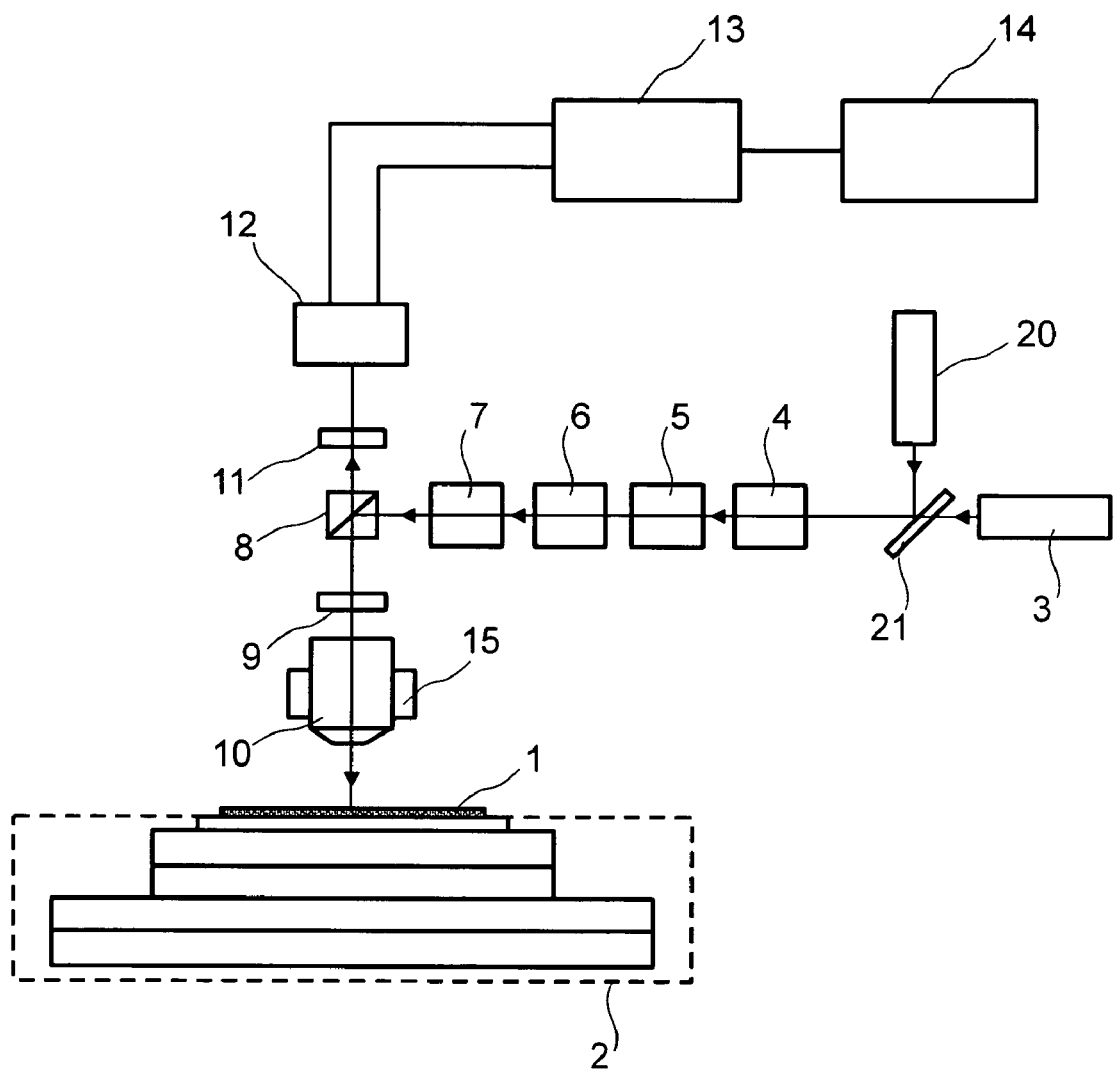
FIG. 34 is a block diagram showing another embodiment of this invention.

Another embodiment of the pattern-defect inspection apparatus according to this invention is shown in FIG. 34. The pattern-defect inspection apparatus of this embodiment consists of: the conveyance system 2 for placing and moving the wafer 1 to be inspected, the illumination light source 3, the pseudo continuous-wave forming optical system 4, the beam formation optical system 5, the coherence reduction optical system 6, the deformation illumination optical system 7, the PBS 8, the light modulation unit A 9, the objective lens 10, the light modulation unit B 11, the visual-field divided parallel detection unit 12, the signal processing circuit 13, the I/O unit 14, the A/F unit 15, an illumination light source 20 having a wavelength different from that of the illumination light source 3, a dichroic prism 21, and controllers, relay lenses, and mirrors of the units not shown in the figure.

Next, its operation will be described. The illumination light of a wavelength λ1 emitted from the illumination light source 3 and the illumination light of a different wavelength λ2 emitted from the illumination light source 20 are combined to share the same optical path by the dichroic prism 21. The combined illumination light enters the pseudo continuous-wave forming optical system 4, where the amount of light is averaged or almost equalized temporally. As in the case of the embodiment 1, the illumination light emitted from the pseudo continuous-wave forming optical system 4 enters the beam formation optical system 5, where its beam diameter and illuminance distribution are adjusted. This illumination light emitted from the beam formation optical system 5 enters the coherence reduction optical system 6, where its temporal and spatial coherence is reduced. The illumination light emitted from the coherence reduction optical system 6 is made to change its illuminance distribution in the pupil position of the objective lens 10 by the deformation illumination optical system 7. The S-polarization component of the illumination light emitted from the deformation illumination optical system 7 is reflected to the objective lens 10 side by the PBS 8, and irradiated on the wafer 1 through the light modulation unit A 9 and the objective lens 10.

The illumination light irradiated on the wafer 1 is diffracted by the wafer 1, focused by the objective lens 10, and enters the PBS 8 through the light modulation unit A 9. The P-polarization component of the incident light is transmitted through the PBS 8, and forms an image on the image sensor in the visual-field divided parallel detection unit 12 through the light modulation unit B 11. The image sensor converts it to an image signal. The image signal thus converted is subjected to defect detection processing in the signal processing circuit 13, which detects defects on the wafer 1. By making the conveyance system 2 move the wafer 1, the above processing is executed on the whole surface of the wafer 1, and inspection results are displayed in the I/O unit 14. This I/O unit 14 has an interface function of receiving input information from the user, and enables transmission and reception of control signals to the controllers. In addition, the A/F unit 15 emits a signal for moving the wafer 1 to the focal position of the objective lens 10, and controls the conveyance system 2 with the controller to move the wafer 1 in real time.

Here, the PBSs, the objective lens, and the imaging optical system that are used in this configuration are optimized so that good performance can be obtained at wavelengths λ1 and λ2, and operations after the pseudo continuous-wave forming optical system 4 may be the same as those in the embodiment 1.

Figure 35:
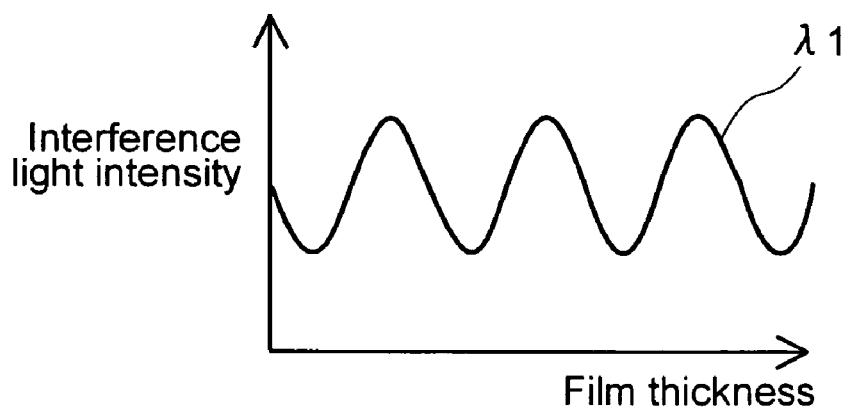
FIG. 35A is a diagram of a relation of interference light intensity of reflected light versus the thickness of a transparent film with a single wavelength used.
FIG. 35B is a diagram of a relation of interference light intensity of reflected light versus the thickness of a transparent film with two wavelengths used.
Figure 35:
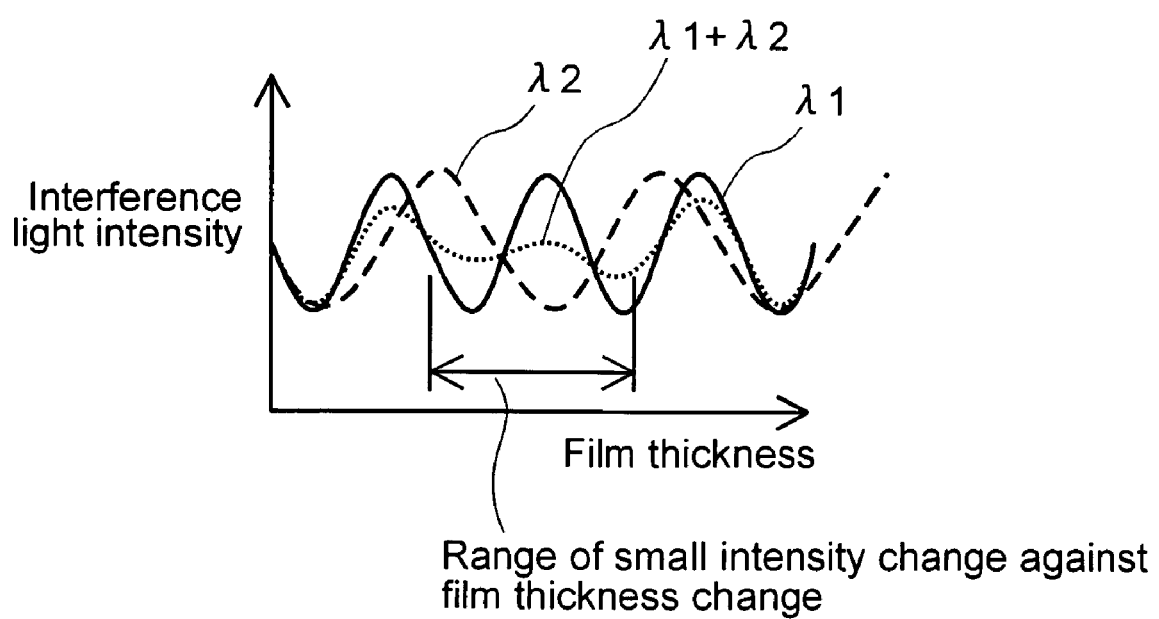

The object of this embodiment is to provide a high-sensitivity pattern-defect inspection apparatus by reducing the thin film interference arising from the transparent thin film, such as an insulator film, formed on an LSI and by decreasing the wavelength dependence of detected defects arising from the interference of light. FIG. 35 shows a relation of the interference light intensity of the reflected light versus the thickness of the transparent film. FIG. 35A shows a case of a single wavelength (wavelength λ1). As shown in FIG. 35A, interference light intensity changes in the form of a sinusoidal wave as a function of film thickness. When the film thickness t satisfies Formula 9, the intensity becomes large, and when satisfying Formula 10, the intensity becomes small. In Formula 9 and Formula 10, the wavelength of the illumination light is indicated by λ, and n is an integer.

$$T=\lambda \times n \text{ or } t=\lambda \times n+\lambda/2 \qquad \text{(Formula 9)}$$

$$T=\lambda \times n+\lambda/4, \text{ or } t=\lambda \times n+\lambda \times \tfrac{1}{8} \qquad \text{(Formula 10)}$$

As can be understood from Formula 9 and Formula 10, at a single wavelength, as the wavelength λ becomes short, a variation in the interference intensity becomes sensitive to change in the film thickness.

To illustrate this, FIG. 35B shows the interference light intensity in the case where light of wavelength λ1 is added with light of different wavelength λ2. When light of wavelength λ2 is irradiated alone, the variation in the interference intensity as described above will appear. When the light is increased to two having different wavelengths, the interference intensity is averaged temporally and a film thickness range of small interference intensity change against film thickness change can be created. Considering a manufacture range of film thickness in the LSI, a wavelength that reduces this change in the interference intensity is chosen as that of the second light source, whereby an inspection apparatus insensitive to interference can be provided. To give one example of such wavelengths, when the wavelength of the first light source is 266 nm, it is recommended to set the wavelength of the second light source to 355 nm.

Embodiment 4

Figure 36:
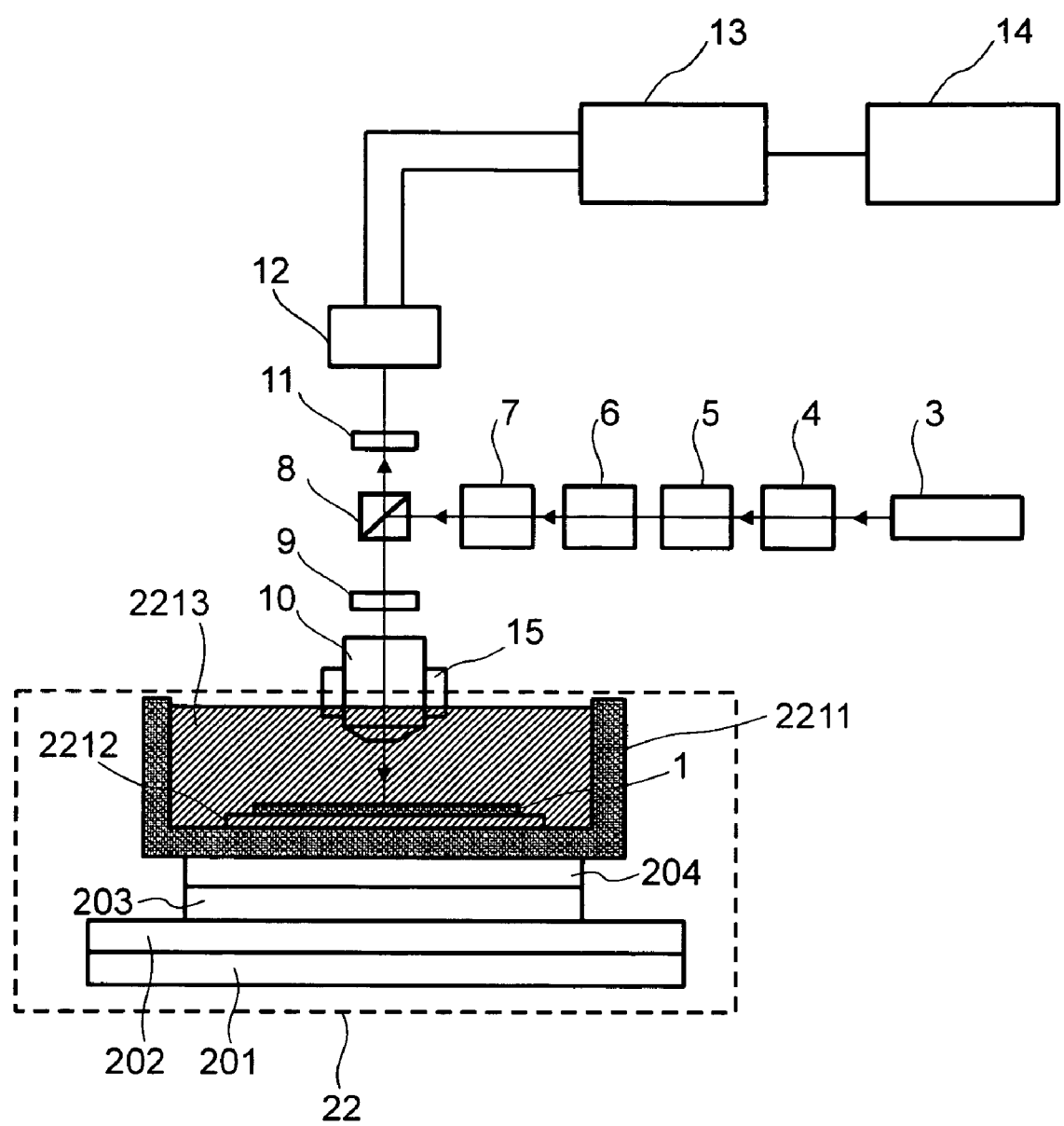
FIG. 36 is a block diagram showing another embodiment of this invention.

Another embodiment of the pattern-defect inspection apparatus according to this invention is shown in FIG. 36. The pattern-defect inspection apparatus of this embodiment is constructed with: an oil-immersion conveyance system 22 for moving the wafer 1 to be inspected that is placed thereon while being immersed in a medium 2213, the illumination light source 3, the pseudo continuous-wave forming optical system 4, the beam formation optical system 5, the coherence reduction optical system 6, the deformation illumination optical system 7, the PBS 8, the light modulation unit A 9, an objective lens 10', the light modulation unit B 11, the visual-field divided parallel detection unit 12, the signal processing circuit 13, the I/O unit 14, and the A/F unit 15, as well as controllers, relay lenses, and mirrors of the units not shown in the figure. The objective lens 10' differs from the objective lens 10 shown in FIG. 1 in that it has a sealed structure such that the medium 2213 does not leak into the inside when being immersed in the medium 2213.

The oil-immersion conveyance system 22 consists of the X-axis stage 201, the Y-axis stage 202, the Z-axis stage 203, the θ-axis stage 204, a medium reservoir part 2211, and an oil-immersion wafer chuck 2212. The X-axis stage 201 is constructed to be able to travel at a constant speed, and the Y-axis stage is constructed to be able to move stepwise. By using the X-axis stage 201 and the Y-axis stage 202, all locations in the wafer 1 can be moved to just under the center of the objective lens 10'. The Z-axis stage 203 has a function of moving vertically the medium reservoir part 2211 and the oil-immersion wafer chuck 2212. The θ-axis stage 204 has a function of rotating the medium reservoir part 2211 and/or the oil-immersion wafer chuck 2212, and aligning the traveling directions of the X-axis stage 201 and the Y-axis stage 202 with the rotation direction of the wafer 1.

The medium reservoir part 2211 is a part that reserves the medium 2213 whose refractive index is different from air, such as pure water, and keeps on reserving it even when the X-axis stage 201 and the Y-axis stage 202 are in motion. Regarding the limit to which the medium is reserved, any limit will do as long as the medium can be charged between the wafer 1 and the objective lens 10'. The medium reservoir part 2211 has a function of allowing the medium to be poured and discharged (not shown in the figure). Here, the medium 2213 should have a refractive index larger than that of air (refractive index>1, preferably the refractive index being close to the refractive index of SiO2 at the illumination wavelength) and should not cause damage to the wafer 1. For example, pure water used regularly in semiconductor factories may be used for this.

Figure 37:
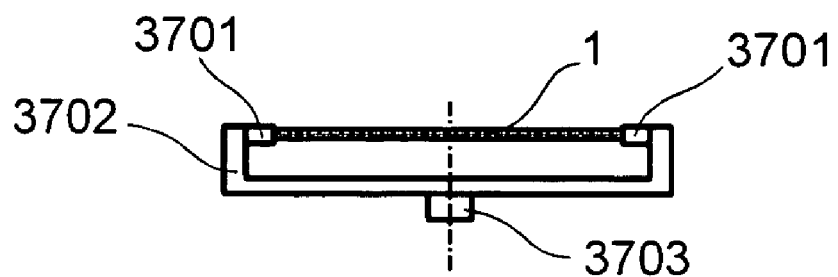
FIG. 37 is a view showing a holding method of a sample.
Figure 37:
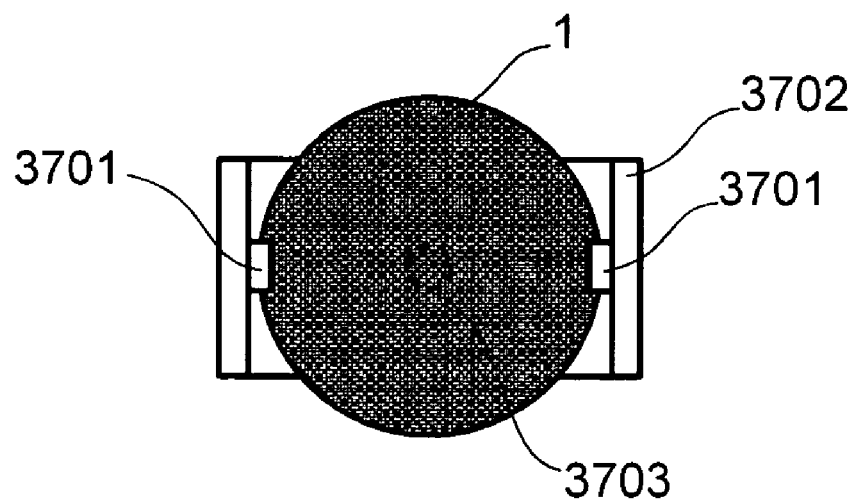

The oil-immersion wafer chuck 2212 has a function of fixing the wafer 1 and is made of a material resistant to corrosion by the medium 2213. A method for fixing the wafer 1 may be, for example, to suck the wafer 1 by means of vacuum before immersing the wafer 1 in the medium 2213. Alternatively, the method may be a method of holding edge parts of the wafer 1, as shown in FIG. 37. A mechanism of FIG. 37 consists of nails 3701 for holding the wafer 1, a nail holder 3702 for holding the nails 3701, and a rotary shaft 3703 for rotating the nail holder 3702. Here, the nail 3701 has a function of catching an edge part of the wafer 1 from the upper and lower sides, and the nail holder 3702 has a function of linking the nails 3701 and the rotary shaft 3703.

Next, its operation will be described. The illumination light emitted from the illumination light source 3 enters the pseudo continuous-wave forming optical system 4, where its amount of light is averaged or almost equalized temporally. As in the case of the embodiment 1, the illumination light emitted from the pseudo continuous-wave forming optical system 4 enters the beam formation optical system 5, where its beam diameter and illuminance distribution are adjusted. This illumination light emitted from the beam formation optical system 5 enters the coherence reduction optical system 6, where its temporal and spatial coherence is reduced. The deformation illumination optical system 7 changes an illuminance distribution of the illumination light emitted from the coherence reduction optical system 6 in a position of the pupil of the objective lens 10'. The S-polarized light component of the illumination light emitted from the deformation illumination optical system 7 is reflected by the PBS 8 to the objective lens 10' side, and is irradiated on the wafer 1 through the light modulation unit A 9 and the objective lens 10'.

The illumination light irradiated on the wafer 1 is diffracted by the wafer 1, and the diffracted light is focused by the objective lens 10' and transmitted through the light modulation unit A 9 to enter the PBS 8. The P-polarized light component of the incident light is transmitted through the PBS 8, forms an image on the image sensor in the visual-field divided parallel detection unit 12 through the light modulation unit B 11. The image sensor converts it to an image signal. The image signal thus converted is subjected to defect detection processing in the signal processing circuit 13, which detects defects on the wafer 1. By making the oil-immersion conveyance system 22 move the wafer 1, the above processing is executed on the whole surface of the wafer 1, and inspection results are displayed in the I/O unit 14. This I/O unit 14 has an interface function of receiving input information from the user, and enables transmission and reception of control signals to the controllers. In addition, the A/F unit 15 emits a signal for moving the wafer 1 to the focal position of the objective lens 10', and controls the conveyance system 2 with the controller to move the wafer 1 in real time.

The object of this embodiment is to provide a high-sensitivity pattern defect inspection apparatus that is embodied with both optical noise reduction realized by reducing thin film interference arising from a transparent thin film, such as an insulator film, formed on an LSI and increase in resolution realized by enlarging the NA of the objective lens.

A principle of achievement of the effect will be described. Originally, thin film interference occurs at an interface at which the refractive index changes. For example, when light is incident on an insulator film of a refractive index of 1.5, thin film interference occurs at the interface with air of a refractive index of unity. The feature of this embodiment is that air between the objective lens and the sample is removed, a medium of a refractive index of about 1.5 is charged there in place of air to get rid of a part at which the refractive index changes, so that thin film interference is reduced. The NA of the objective lens is given by Formula 11, and accordingly varies with the refractive index of the medium between the objective lens and the sample. Therefore, as described above, when the refractive index of a medium between the objective lens and the sample is made large, the NA can be increased and hence high-resolution detected image will be able to be obtained.

$$NA = n \times \sin\theta \quad \text{(Formula 11)}$$

(Here, n is a refractive index of the medium between the objective lens and the sample, and θ is the angular aperture of the objective lens.)

If the apparatus is configured as described in the foregoing, the apparatus can inspect defects of various LSI patterns at high speed and with high sensitivity. Incidentally, the contents described in each embodiment can also be used in any of the other embodiments.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An apparatus for detecting defects of a sample, comprising:

an illumination light source that emits pulsed ultraviolet laser light;

a polarized light splitter unit that splits each pulse of the pulsed ultraviolet laser light emitted from the illumination light source into plural pulses of P-polarized laser light and S-polarized laser light;

an irradiating unit that selectively irradiates a sample with the split ultraviolet P-polarized and S-polarized ultraviolet laser light split by the polarized light splitter unit from a perpendicular direction with the split S-polarized ultraviolet laser light and from an oblique direction to the sample with the split P-polarized ultraviolet laser light;

a light detecting unit that detects light from the sample irradiated with the split polarized ultraviolet laser light by the selected oblique irradiation of the irradiating unit with the split P-polarized ultraviolet laser and by the selected perpendicular irradiation of the irradiating unit with the split S-polarized ultraviolet laser light; and a defect detecting unit that detects defects of the sample by processing a signal outputted from the light detecting unit which includes a dark field signal obtained by separately detecting the light from the sample caused by the selected oblique irradiation with the split P-polarized ultraviolet laser light and a bright field signal obtained by separately detecting the light from the sample caused by the selected perpendicular irradiation with the split S-polarized ultraviolet laser light.

2. The apparatus according to claim 1, further comprising an amount-of-light distribution adjusting unit that adjusts an in-plane distribution of an amount of the pulsed ultraviolet laser light emitted from the illumination light source, the amount-of-light distribution adjusting unit being disposed in an optical path from the illumination light source to the irradiating unit.

3. The apparatus according to claim 1, further comprising a deformation illuminating unit that deflects the pulsed ultraviolet laser light emitted from the illumination light source, the deformation illuminating unit being disposed in an optical path from the illumination light source to the irradiating unit.

4. The apparatus according to claim 1, further comprising a light modulating unit that controls the light from the sample on which the pulsed ultraviolet laser light is irradiated, the light modulating unit being disposed in an optical path from the illumination light source to the irradiating unit.

5. The apparatus according to claim 1, wherein the irradiating unit passes the split S-polarized ultraviolet laser light through an objective lens to irradiate the sample in the perpendicular direction with the S-polarized ultraviolet light and passes the split P-polarized ultraviolet laser light outside of the objective lens to irradiate the sample in the oblique direction with the P-polarized ultraviolet light, and the light detecting unit detects the light caused by the perpendicular irradiation of the sample which is passed through the objective lens and detects the light caused by the oblique irradiation of the sample which is passed through the objective lens.

6. A method for detecting defects of a sample, comprising the steps of:
  reducing a peak intensity level of pulsed ultraviolet laser emitted from a light source by splitting each pulse of the pulsed ultraviolet laser light into plural pulses of P-polarized ultraviolet laser light and S-polarized ultraviolet laser light while maintaining its total amount per unit time;
  selectively irradiating the peak intensity level reduced polarized ultraviolet laser light on a sample from a perpendicular direction with the split S-polarized ultraviolet laser light and from an oblique direction with the split P-polarized ultraviolet laser light;
  detecting light from the sample illuminated by the step of selectively irradiating the sample from the oblique direction with the split P-polarized ultraviolet laser light and from the perpendicular direction with the split S-polarized ultraviolet laser light;
  detecting defects of a surface of the sample by processing a signal obtained at the detecting step by the detection of the light from the sample which includes a dark field signal obtained by detecting the light from the sample caused by the selected irradiation of the light in the oblique direction with the split P-polarized ultraviolet laser light and a bright field signal obtained by detecting the light from the sample caused by the selected irradiation of the light in the perpendicular direction with the split S-polarized ultraviolet laser light;
  classifying the defects thus detected; and
  displaying information of a defect detected at the detecting step and at the classifying step.

7. The method according to claim 6, wherein the peak intensity level reduced polarized ultraviolet laser irradiated on the sample is adjusted in terms of a distribution of the amount of light in a cross section of the pulsed ultraviolet laser light.

8. The method according to claim 6, wherein the peak intensity level reduced polarized ultraviolet laser light irradiated on the sample is adjusted for a distribution of its amount of light to be in the form of a circular band in a position of a pupil of an objective lens.

9. The method according to claim 6, wherein the step of irradiating the split S-polarized ultraviolet laser light on the sample from the perpendicular direction includes passing the pulsed ultraviolet laser light through an objective lens for irradiation on the sample from the perpendicular direction with the S-polarized ultraviolet light, the step of irradiating the split P-polarized ultraviolet laser light on the sample from the oblique direction includes irradiation of the P-polarized ultraviolet laser light on the sample from the oblique direction with the P-polarized ultraviolet light without passing through the objective lens, and the step of detecting the light from the sample includes detecting light passed through the objective lens in response to the sample being illuminated by the step of irradiating from the perpendicular direction and detecting light passed through the objective lens in response to the step of irradiating from the oblique direction.

* * * * *